US012678761B2

(12) United States Patent
Manning et al.

(10) Patent No.: US 12,678,761 B2
(45) Date of Patent: Jul. 14, 2026

(54) GAS-TO-LIQUID REACTOR AND METHOD OF USING

(71) Applicant: PlasMerica, LLC, Miami, OK (US)

(72) Inventors: Dennis Keith Manning, Miami, OK (US); Arland H. Johannes, Stillwater, OK (US)

(73) Assignee: PlasMerica, LLC, Miami, OK (US)

( * ) Notice: Subject to any disclaimer, the term of this patent is extended or adjusted under 35 U.S.C. 154(b) by 16 days.

(21) Appl. No.: 18/623,477

(22) Filed: Apr. 1, 2024

(65) Prior Publication Data

US 2024/0326006 A1 Oct. 3, 2024

Related U.S. Application Data

(63) Continuation of application No. 16/989,522, filed on Aug. 10, 2020, now Pat. No. 11,944,950, which is a (Continued)

(51) Int. Cl.
*B01J 19/08* (2006.01)
*C07C 2/80* (2006.01)

(52) U.S. Cl.
CPC ............... *B01J 19/088* (2013.01); *C07C 2/80* (2013.01); *B01J 2219/0809* (2013.01); (Continued)

(58) Field of Classification Search
CPC .............. B01J 19/088; B01J 2219/0809; B01J 2219/0813; B01J 2219/083; B01J 2219/0875; B01J 2219/0892; B01J 2219/0896; B01J 2219/0869; B01J 19/129; B01J 19/126; B01J 19/128; B01J 19/121;
(Continued)

(56) References Cited

U.S. PATENT DOCUMENTS

| | | | |
|---|---|---|---|
| 2,664,394 | A | 12/1953 | Byron |
| 4,975,164 | A | 12/1990 | Ravella |

(Continued)

FOREIGN PATENT DOCUMENTS

| | | | |
|---|---|---|---|
| JP | 5328008 | B2 | 10/2013 |
| RU | 2190659 | C2 | 10/2002 |

(Continued)

OTHER PUBLICATIONS

Chemical encyclopedia under the editorship of I.L. Knunyants, M. 1992, vol. 3, col. 345.

(Continued)

*Primary Examiner* — Xiuyu Tai
(74) *Attorney, Agent, or Firm* — Knobbe Martens Olson & Bear, LLP

(57) ABSTRACT

A device and a process to propagate molecular growth of hydrocarbons, either straight or branched chain structures, that naturally occur in the gas phase to a molecular size sufficient to shift the natural occurring phase to a liquid or solid state is provided. According to one embodiment, the device includes a grounded reactor vessel having a gas inlet, a liquid outlet, and an electrode within the vessel; a power supply coupled to the electrode for creating an electrostatic field within the vessel for converting the gas to a liquid and or solid state.

19 Claims, 16 Drawing Sheets

Related U.S. Application Data continuation of application No. 15/905,674, filed on Feb. 26, 2018, now Pat. No. 10,737,235, which is a continuation of application No. PCT/US2016/049757, filed on Aug. 31, 2016.

(60) Provisional application No. 62/214,717, filed on Sep. 4, 2015.

(52) U.S. Cl.
CPC .. *B01J 2219/0813* (2013.01); *B01J 2219/083* (2013.01); *B01J 2219/0875* (2013.01); *B01J 2219/0892* (2013.01); *B01J 2219/0896* (2013.01)

(58) Field of Classification Search
CPC ........ B01J 2219/0871; B01J 2219/0854; B01J 2219/0883; B01J 19/087; B01J 2219/0852; B01J 2219/0295; B01J 2219/0811; B01J 2219/0818; B01J 2219/0263; C07C 2/80; C10G 50/00; C10G 2400/08; C10G 2400/04; C10G 2400/06; C10G 2300/1025; C10G 2400/02; C10G 2/00; C01B 2203/1241; C01B 2203/0272; C01B 3/24; C01B 32/05; H05H 1/46; H05H 1/4645; H05H 1/461
See application file for complete search history.

(56) References Cited

U.S. PATENT DOCUMENTS

| | | | | |
|---|---|---|---|---|
| 5,277,773 | A | 1/1994 | Murphy | |
| 5,328,577 | A | 7/1994 | Murphy | |
| 5,749,937 | A | 5/1998 | Detering | |
| 6,007,742 | A | 12/1999 | Czernichowski | |
| 6,284,105 | B1 | 9/2001 | Eliasson | |
| 6,326,407 | B1 * | 12/2001 | Eliasson ................ | C10G 50/00 518/715 |
| 7,510,632 | B2 | 3/2009 | Denes | |
| 10,737,235 | B2 | 8/2020 | Manning | |
| 2004/0200731 | A1 | 10/2004 | Sullivan | |
| 2008/0038162 | A1 | 2/2008 | Koshiishi et al. | |
| 2009/0205254 | A1 * | 8/2009 | Zhu ........................ | B01J 19/088 48/127.9 |
| 2010/0296980 | A1 | 11/2010 | Nakatani | |
| 2011/0190565 | A1 | 8/2011 | Novoselov | |
| 2014/0239232 | A1 | 8/2014 | Staton | |
| 2015/0041309 | A1 | 2/2015 | Spitzi | |
| 2015/0158008 | A1 * | 6/2015 | Wong ..................... | C10G 50/00 422/186.03 |
| 2015/0218474 | A1 | 8/2015 | Lynch | |
| 2016/0030912 | A1 | 2/2016 | Mango | |
| 2016/0296905 | A1 | 10/2016 | Kuhl | |

FOREIGN PATENT DOCUMENTS

| | | | |
|---|---|---|---|
| WO | WO 2017/040704 | A1 | 3/2017 |
| WO | WO 2017/050704 | A1 | 3/2017 |

OTHER PUBLICATIONS

Fincke et al., "Plasma pyrolysis of methane to hydrogen and carbon black," Industrial & Engineering Chemistry Research, 41:1425-1435 (2002).
Goncharov, V., M. A. Veklich, and V. V. Lopatin. "Conversion of associated petroleum gas into liquid hydrocarbons in barrier discharge plasma." SPE Russian Oil and Gas Technical Conference and Exhibition. OnePetro, 2008.
Whitehead, J. Christopher, and Maria Prantsidou. "Investigation of hydrocarbon oil transformation by gliding arc discharge: comparison of batch and recirculated configurations." Journal of Physics D: Applied Physics 49.15 (2016): 154001.
International Search Report and Written Opinion dated Dec. 1, 2016 for PCT/US2016/049757, filed Aug. 31, 2016.
International Preliminary Report on Patentability dated Mar. 6, 2018 2015 for PCT/US2016/049757, filed Aug. 31, 2016.
International Search Report dated Jul. 5, 2020, issued in International Application No. PCT/US2019/027345.

* cited by examiner

GAS-TO-LIQUID REACTOR AND METHOD OF USING

INCORPORATION BY REFERENCE TO RELATED APPLICATIONS

Any and all priority claims identified in the Application Data Sheet, or any correction thereto, are hereby incorporated by reference under 37 CFR 1.57. This application is a continuation of U.S. patent application Ser. No. 16/989,522, filed Aug. 10, 2020, which is a continuation of U.S. patent application Ser. No. 15/905,674, filed Feb. 26, 2018, which is a continuation of PCT International Application No. PCT/US2016/049757, filed Aug. 31, 2016, which claims the benefit of U.S. Provisional Application No. 62/214,717, filed Sep. 4, 2015. Each of the aforementioned applications is incorporated by reference herein in its entirety, and each is hereby expressly made a part of this specification.

TECHNICAL FIELD

A production-worthy reactor and methods to propagate molecular growth of hydrocarbons, either straight or branched chain structures, that naturally occur in the gas phase to a molecular size sufficient to shift the natural occurring phase to that of a liquid or solid state are provided.

BACKGROUND

Short chain hydrocarbons exist in many species and configurations. The most common natural occurring gaseous hydrocarbon, methane, is a single carbon surrounded by four hydrogen atoms. This molecule is abundantly found in natural gas reservoirs, generated from decaying plant and animal matter and is a very strong greenhouse gas. The abundance, low cost and negative environmental aspects make this gas of particular interest in the energy, chemical processing and environmental industries. For example, the energy market has continuously sought methods to increase the value of gaseous phase hydrocarbons through conversion to a liquid state. Likewise, specialty and fine chemical producers continue to seek low material cost avenues. Of equal importance, these industries and others have sought ways to convert waste gas streams into marketable liquid or solid products, through chain propagation.

Many such conversion opportunities exist where venting, flaring and re-injection techniques are presently deployed. For example, vented gas from landfills or co-produced at crude oil production sites, flared gas at oil and gas production sites and re-injected gas sites all offer potential economic interest. In addition the value increase from converting low value gas phase materials to liquid petroleum or solid compounds to be used as products, feedstocks or potential fuels has economic justification. Furthermore, and as significant from an environmental perspective, the environmental market has sought and continues to seek methodologies to eliminate the venting or flaring of gas products from landfills, bio-generation systems and waste management situations. Some additional areas of interest are associated with chemical processing sites, low to medium gas production sites, stranded gas situations and abandoned wells or coal bed methane and the like. Thus, opportunities arise from both economic interests and environmental concerns.

Numerous devices to propagate molecular chain growth in hydrocarbons have been developed and utilized with mixed results. In the past, attention has focused on conversion based upon the Fisher-Tropsch technology. In addition, the conversion of natural gas to hydrocarbons by high temperature, combustion heating, pyrolysis; microwave technology; electromagnetic radiation; electrical discharge; the use of a catalyst and non-catalytic oxidation techniques have been suggested. Some have suggested first heating the gas to convert a portion thereof to hydrogen and then using a catalyst to promote propagation. Specifically, patents such as U.S. Pat. No. 3,389,189, relating to pyrolysis; U.S. Pat. No. 5,277,773, relating to the use of microwaves; U.S. Pat. No. 6,602,920, relating to combustion heating; U.S. Pat. Nos. 7,667,085 and 7,915,463, relating to heating the gas and the use of a catalyst; and U.S. Pat. No. 8,277,631, relating to a plasma assisted electrolytic reaction have met with mixed results especially with regard to scalability to address remote, small generation sites.

A thesis submitted to the Faculty of the Graduate College of the Oklahoma State University directed to "Hydrocarbon Rearrangements and Synthesis Using an Alternating Current Silent Glow Discharge Reactor", on file at the Oklahoma State University Library, North Boomer Annex, OSU Thesis Collection, Thesis 1993 M283h, discusses the fundamentals of hydrocarbon pyrolysis. However, many practical problems were not resolved, such as, the efficiency of limited conversion of gas to liquid phase, nor was the utilization understood or defined. More significantly, the hazardous aspects of the device disclosed in the thesis, especially in view of oil and gas industrial health and safety conditions arising from the high voltage gradients involved in the device were not addressed. In addition, the possibility of an explosive reaction, and electrical shock to field personnel, as well as the limited physical aspects of the reactor itself, all of concern in the oil and gas environment, were not addressed. Furthermore, the chemical species within the liquid phase were not identified, nor were the impacts of operating parameters to component mix or formation rate correlated.

SUMMARY

Although a broad range of methods for converting a gas or natural gas to a liquid are known, problems still exist with regard to the development of an efficient, cost effective, gas field safe, and generally safe, device and related methods for commercial industrial applications. The device and the processes provided are believed to overcome the drawbacks of the known methods as well as to provide a substantial improvement in the conversion of natural hydrocarbon gases to optionally modified liquid and solid phase hydrocarbons.

It is thus desirable to overcome the deficiencies of existing methods to thereby provide a device and processes for converting gaseous hydrocarbons to readily transportable upgraded liquids, such as liquid petroleum, or solids. As used herein, a "liquid state" comprises hydrocarbons and/or modified hydrocarbons of various molecular lengths, as desired by the intended use of the liquid. As used herein, a "solid state" comprises hydrocarbons and/or modified hydrocarbons of various molecular lengths, which can be selected according to the intended use of the solid. For the sake of clarity, the device and processes disclosed herein may be utilized to generate an optionally modified hydrocarbon liquid having a preselected or desired vapor pressure range or a solid material composed of high molecular weight hydrocarbon species.

In addition, it is desirable to process natural gas reserves, which are currently not being utilized due to their location, either away from an existing gas pipeline or isolated by the cost to build one out to the reserve. Currently, re-injection of the gas into the well, and gas flaring or venting are inefficient and wasteful dispositions of readily, available natural gas. These inefficiencies and cost-ineffective or wasteful uses are overcome by the methods and apparatus of various embodiments.

Methods and apparatus of various embodiments can also be employed to process vented gas from landfills and other locations, or to reclaim and/or process chemical processing plant gas by-products, which are currently subjected to destruction.

In one embodiment, a device for propagating molecular growth of hydrocarbons, either straight or branched chain structures, that naturally occur in the gas phases to a molecular size sufficient to shift the natural occurring phase to a liquid or solid state comprises an electrically charged or grounded vessel having an inlet, an outlet and an electrode within the vessel; and a power supply coupled through the vessel to the electrode.

In another embodiment, a device for converting a gas to a liquid or solid state comprises an electrically charged or grounded vessel having an inlet, an outlet and multiple electrodes within the vessel; and a power supply coupled through the vessel to some of the electrodes, other of the electrodes being coupled to ground. Accordingly, the use of the term “an electrode” encompasses multiple electrodes herein.

In another embodiment, a device for converting a gas to a liquid or solid state comprises an electrically charged or grounded vessel having an inlet, an outlet and an electrode within the vessel; and a variable voltage power supply coupled through the vessel to the electrode.

In another embodiment, a device for converting a gas to a liquid or solid state comprises an electrically charged or grounded vessel having an inlet, an outlet and an electrode within the vessel; and a variable frequency power supply coupled through the vessel to the electrode.

In another embodiment, a gas is subjected to an electrostatic field creating a plasma for promoting molecular growth and/or converting the gas to a liquid and/or solid.

In another embodiment, a gas is subjected to an electrostatic field of variable frequency creating a plasma for promoting molecular growth and/or converting the gas to a liquid and/or solid.

In another embodiment, a gas is subjected to an electrostatic field of variable voltage creating a plasma for promoting molecular growth and/or converting the gas to a liquid and/or solid.

Accordingly, in a generally applicable first aspect (i.e., independently combinable with any of the aspects or embodiments identified herein), a method for synthesizing a liquid hydrocarbon, a solid hydrocarbon, or a combination thereof, comprising a first compound of Formula I is provided, comprising: providing a gas phase hydrocarbon; and subjecting the gas phase hydrocarbon to a plasma created by an electrostatic field, whereby a first compound of Formula I is produced; wherein in Formula (I), m is an integer from 0 to 40, each $R^1$ and $R^2$ is independently selected from the group consisting of hydrogen and a linear, branched, or cyclic hydrocarbon moiety of one to twenty carbon atoms, or each $R^1$ and corresponding $R^2$ and the atoms to which they attach are joined to form a cyclic hydrocarbon moiety of 1 to 8 carbon atoms, and Z is hydrogen or methyl.

In an embodiment of the first aspect (i.e., independently combinable with any of the aspects or embodiments identified herein), m can be an integer from 1 to 20.

In an embodiment of the first aspect (i.e., independently combinable with any of the aspects or embodiments identified herein), m can be an integer from 5 to 8.

In an embodiment of the first aspect (i.e., independently combinable with any of the aspects or embodiments identified herein), each $R^1$ and each $R^2$ can be independently selected from the group consisting of hydrogen, methyl, and ethyl.

In an embodiment of the first aspect (i.e., independently combinable with any of the aspects or embodiments identified herein), the first compound can be selected from butane, 2-methyl-butane, 2-methyl-pentane, n-hexane, 2,2,3-trimethyl-butane, 2-methyl-hexane, 2,3-dimethyl-Pentane, 3-methyl-hexane, 2,4-dimethyl-hexane, 3,3-dimethyl-hexane, 2,3,3-trimethyl-Pentane, 2,3-dimethyl-hexane, 3-methyl-heptane, 2,3,5-trimethyl-hexane, 2,3,3-trimethyl-hexane, 2,3-dimethyl-Heptane, 2,2,4-trimethyl-heptane, 2,4,6-trimethyl-heptane, 4-ethyl-2-methyl-hexane, 2,3,5-trimethyl-heptane, 2,3,6-trimethyl-heptane, and 2,3,5-trimethyl-heptane.

In an embodiment of the first aspect (i.e., independently combinable with any of the aspects or embodiments identified herein), the first compound can be selected from octane, 4-methyl-octane, 3-methyl-octane, 2,4,6-trimethyl-octane, 4,4-dimethyl-octane, 2,5-dimethyl-octane, 2,3,3-trimethyl-octane, 3,4,5,6-tetramethyl-octane, 2,3,6,7-tetramethyl-octane, nonane, 3-methyl-nonane, 4-methyl-nonane, 3-methyl-nonane, decane, 3,6-dimethyl-decane, 2,3,6-trimethyl-decane, and 2,5,9-trimethyl-decane.

In an embodiment of the first aspect (i.e., independently combinable with any of the aspects or embodiments identified herein), the first compound can be selected from undecane, 2,6-dimethyl-undecane, 5,7-dimethyl-undecane, and dodecane.

In an embodiment of the first aspect (i.e., independently combinable with any of the aspects or embodiments identified herein), the first compound can be selected from 2,3,3-trimethyl-pentane, 3,3-dimethyl-hexane, 2,3-dimethyl-hexane, 2-methyl-hexane, 3-methyl-hexane, 2,4-dimethyl-hexane, 2,3-dimethyl-heptane, 4-methyl-octane, 3-methyl-octane, 4,4-dimethyl octane, and 3-methyl-nonane.

In an embodiment of the first aspect (i.e., independently combinable with any of the aspects or embodiments identified herein), the first compound can be obtained as a mixture with a second compound having the structure of Formula (I).

In an embodiment of the first aspect (i.e., independently combinable with any of the aspects or embodiments identified herein), the second compound can be selected from Butane, 2-methyl-Butane, 2-methyl-Pentane, n-Hexane, 2,2,3-trimethyl-Butane, 2-methyl-Hexane, 2,3-dimethyl-Pentane, 3-methyl-Hexane, 2,4-dimethyl-Hexane, 3,3-dimethyl-Hexane, 2,3,3-trimethyl-Pentane, 2,3-dimethyl-Hexane, 3-methyl-Heptane, Octane, 2,3,5-trimethyl-Hexane, 2,3,3-trimethyl-Hexane, 2,3-dimethyl-Heptane, 4-methyl-Octane, 3-methyl-Octane, 2,4,6-trimethyl-Octane, 2,2,4-trimethyl-Heptane, 2,4,6-trimethyl-Heptane, Nonane, 4-ethyl-2-methyl-Hexane, 4,4-Dimethyl-octane, 2,3,5-trimethyl-Heptane, 2,5-dimethyl-Octane, 2,3,6-trimethyl-Heptane, 2,3,5-trimethyl-Heptane, 3-methyl-Nonane, 4-methyl-Nonane, 2,3,3-trimethyl-Octane, Decane, 3,4,5,6-tetramethyl-Octane, 3-methyl-Nonane, 3,6-dimethyl-Decane, 2,5,9-trimethyl-Decane, 2,3,6,7-tetramethyl-Octane, Undecane, 2,6-dimethyl-Undecane, 5,7-dimethyl-Undecane, 2,3,6-trimethyl-Decane, and Dodecane.

In an embodiment of the first aspect (i.e., independently combinable with any of the aspects or embodiments identified herein), the method can further comprise condensing the liquid hydrocarbon, solid hydrocarbon, or combination thereof.

In an embodiment of the first aspect (i.e., independently combinable with any of the aspects or embodiments identified herein), the electrostatic field can be an oscillating field.

In an embodiment of the first aspect (i.e., independently combinable with any of the aspects or embodiments identified herein), the field can oscillate at a frequency from 60 to 1000 Hz.

In an embodiment of the first aspect (i.e., independently combinable with any of the aspects or embodiments identified herein), the field can oscillate at a frequency from 300 to 600 Hz.

In an embodiment of the first aspect (i.e., independently combinable with any of the aspects or embodiments identified herein), the electrostatic field can be from 1000 to 100,000 volts.

In an embodiment of the first aspect (i.e., independently combinable with any of the aspects or embodiments identified herein), the electrostatic field can be from 10,000 to 50,000 volts.

In an embodiment of the first aspect (i.e., independently combinable with any of the aspects or embodiments identified herein), subjecting to a plasma can be conducted at ambient temperature.

In an embodiment of the first aspect (i.e., independently combinable with any of the aspects or embodiments identified herein), subjecting to a plasma can be conducted at a pressure from atmospheric pressure to 100 PSIG.

In an embodiment of the first aspect (i.e., independently combinable with any of the aspects or embodiments identified herein), subjecting to a plasma can be conducted at atmospheric pressure.

In an embodiment of the first aspect (i.e., independently combinable with any of the aspects or embodiments identified herein), the gas phase hydrocarbon can be selected from methane, ethane, n-propane, isopropane, n-butane, isobutane, ethylene, propylene, butylene, acetylene, methylacetylene, ethylacetylene, and mixtures thereof.

In an embodiment of the first aspect (i.e., independently combinable with any of the aspects or embodiments identified herein), the gas phase hydrocarbon can be n-propane.

In an embodiment of the first aspect (i.e., independently combinable with any of the aspects or embodiments identified herein), the method can further comprise isolating the liquid hydrocarbon, solid hydrocarbon, or a combination thereof.

In an embodiment of the first aspect (i.e., independently combinable with any of the aspects or embodiments identified herein), a compound of Formula (I) can be synthesized by the method.

In an embodiment of the first aspect (i.e., independently combinable with any of the aspects or embodiments identified herein), the compound of Formula (I) can be substantially pure.

In a generally applicable second aspect (i.e., independently combinable with any of the aspects or embodiments identified herein), a method for converting a gas to a liquid or a solid is provided, comprising: introducing a gaseous hydrocarbon into a vessel, wherein the vessel is charged or grounded; and subjecting the gaseous hydrocarbon to an electrostatic field creating a plasma, whereby the gaseous hydrocarbon is converted to a liquid hydrocarbon, a solid hydrocarbon, or a combination thereof.

In an embodiment of the second aspect (i.e., independently combinable with any of the aspects or embodiments identified herein), the method can further comprise subjecting the gaseous hydrocarbon to a variable frequency electrostatic field.

In an embodiment of the second aspect (i.e., independently combinable with any of the aspects or embodiments identified herein), the method can further comprise subjecting the gas to a variable voltage electrostatic field.

In an embodiment of the second aspect (i.e., independently combinable with any of the aspects or embodiments identified herein), the method can further comprise subjecting the gas to a variable frequency and a variable voltage electrostatic field.

In an embodiment of the second aspect (i.e., independently combinable with any of the aspects or embodiments identified herein), wherein the gaseous hydrocarbon can have a formula $C_nH_xD_y$ where C is carbon, H is hydrogen, and D is selected from the group consisting of another atom, a portion of a molecule, and a carbon chain, and wherein n, x, and y are each independently an integer>0.

In an embodiment of the second aspect (i.e., independently combinable with any of the aspects or embodiments identified herein), the method can further comprise controlling an amount of gaseous hydrocarbon introduced into the vessel based on a rate of conversion of the gaseous hydrocarbon to a liquid hydrocarbon, a solid hydrocarbon, or a combination thereof.

In an embodiment of the second aspect (i.e., independently combinable with any of the aspects or embodiments identified herein), the method can further comprise controlling an amount of gaseous hydrocarbon introduced into the vessel based on a pressure within the vessel.

In a generally applicable third aspect (i.e., independently combinable with any of the aspects or embodiments identified herein), a method is provided for converting a gaseous hydrocarbon to a liquid hydrocarbon, a solid hydrocarbon, or a combination thereof, substantially as described herein.

In a generally applicable fourth aspect (i.e., independently combinable with any of the aspects or embodiments identified herein), a device is provided for converting a gaseous hydrocarbon to a liquid hydrocarbon, a solid hydrocarbon, or a combination thereof, substantially as described herein.

In a generally applicable fifth aspect (i.e., independently combinable with any of the aspects or embodiments identified herein), a liquid hydrocarbon, a solid hydrocarbon, or a combination thereof is provided, prepared using a device and/or method substantially as described herein.

In a generally applicable sixth aspect (i.e., independently combinable with any of the aspects or embodiments identified herein), a fuel, adhesive, construction material, chemical treatment, solvent, coating, building block for chemical synthesis, preservative, pharmaceutical, personal care product, or refrigerant comprising a liquid hydrocarbon, a solid hydrocarbon, or a combination thereof is provided, prepared using a device and/or method substantially as described herein.

In a generally applicable seventh aspect (i.e., independently combinable with any of the aspects or embodiments identified herein), an isolated liquid hydrocarbon or solid hydrocarbon prepared using a device and/or method substantially as described herein is provided.

In a generally applicable eighth aspect (i.e., independently combinable with any of the aspects or embodiments identified herein), a device for propagating molecular growth of hydrocarbons is provided, comprising: an electrically charged or grounded vessel having an inlet, an outlet and an electrode within the vessel; and a power supply coupled through the vessel to the electrode.

In an embodiment of the eighth aspect (i.e., independently combinable with any of the aspects or embodiments identified herein), the vessel can comprise more than one electrode.

In an embodiment of the eighth aspect (i.e., independently combinable with any of the aspects or embodiments identified herein), the vessel can comprise 1+n electrodes coupled to the power supply and n grounded electrodes, where n is an integer>1.

In an embodiment of the eighth aspect (i.e., independently combinable with any of the aspects or embodiments identified herein), the power supply can be configured to provide a variable frequency source of power.

In an embodiment of the eighth aspect (i.e., independently combinable with any of the aspects or embodiments identified herein), the power supply can be configured to provide a variable voltage supply of power.

In an embodiment of the eighth aspect (i.e., independently combinable with any of the aspects or embodiments identified herein), the power supply can be configured to provide both a variable frequency supply of power and a variable voltage supply of power.

In an embodiment of the eighth aspect (i.e., independently combinable with any of the aspects or embodiments identified herein), the outlet of the vessel can be located at a level below a liquid gas interface of the vessel.

BRIEF DESCRIPTION OF THE DRAWINGS

The details of the present disclosure, both as to its structure and operation, may be understood in part by study of the accompanying drawings, in which like reference numerals refer to like parts. The drawings are not necessarily to scale, emphasis instead being placed upon illustrating the principles of the disclosure.

DETAILED DESCRIPTION

Figure 1:
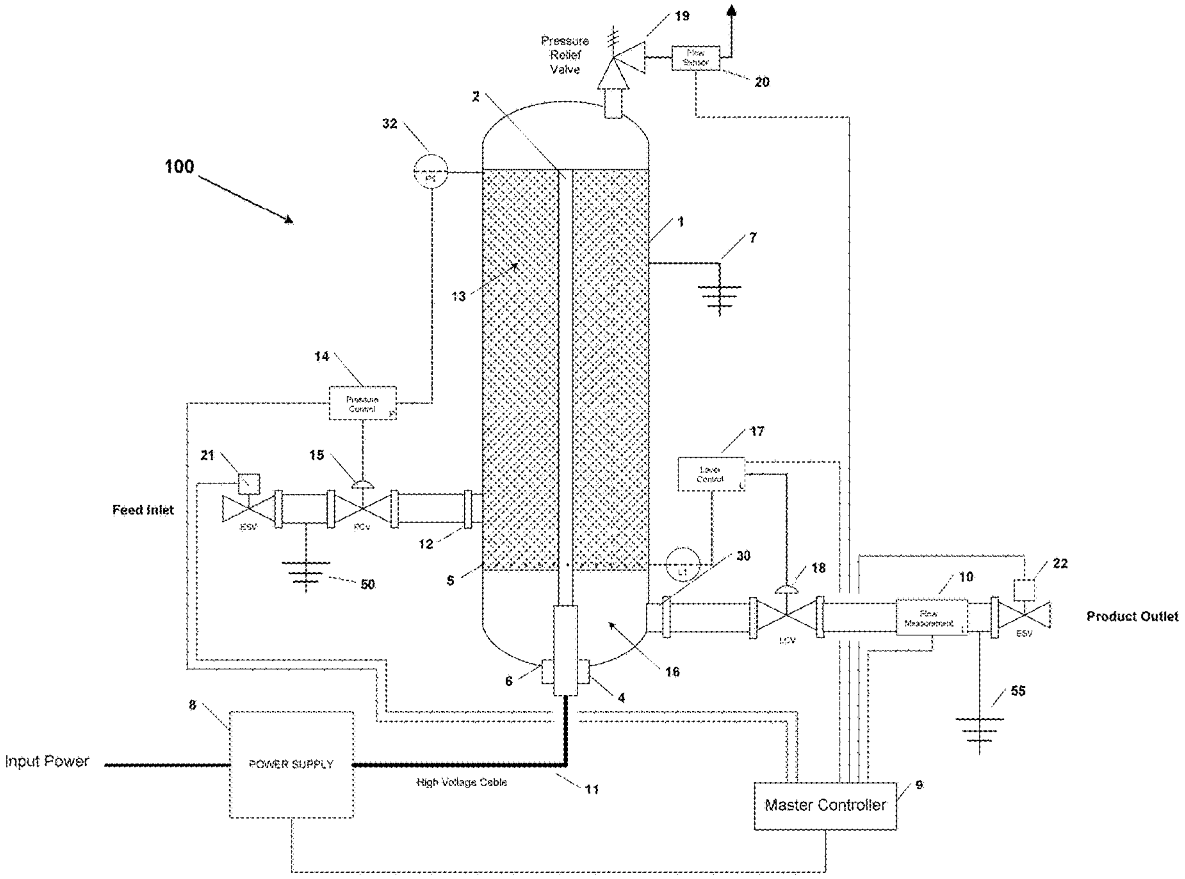
FIG. 1 is a schematic of a preferred embodiment of the device of an embodiment.

As used herein, "hydrocarbon" is employed to describe a molecule containing only carbon and hydrogen atoms. Hydrocarbons can include alkyl, alkenyl, or alkynyl groups, and can include straight or branched chains, and acyclic or cyclic moieties. Although in preferable embodiments, liquid hydrocarbons can be present, the term "hydrocarbon" includes vapors, gases and solid materials.

The words "gas" and "short-chained hydrocarbons" are used interchangeably herein to describe hydrocarbons that are gases at standard conditions (ambient temperature (20° C.) and atmospheric pressure). Such gases include but are not limited to methane ($CH_4$), ethane ($C_2H_6$), propane ($C_3H_8$, including isopropane and n-propane), butane ($C_4H_{10}$, including isobutane and n-butane), ethylene ($C_2H_2$), propylene ($C_3H_6$), butylene ($C_4H_8$), acetylene ($C_2H_2$), methylacetylene, ($C_3H_4$), and ethylacetylene ($C_4H_6$).

The word "liquid" is used herein to describe such liquid hydrocarbons, as well as other petrochemical liquids that contain carbon, hydrogen, and optionally other atoms (such as O, N, S) or functional groups (such as hydroxyls, amines, carbonyls, sulfoxides, thiols, etc.), including modified hydrocarbons. Generally, as provided herein, a liquid exists substantially as a liquid at standard conditions, ambient temperature (20° C.) and atmospheric pressure. However, such a liquid may have a substantial vapor pressure under such conditions. As provided herein, a liquid hydrocarbon and a modified hydrocarbon include those having cyclic moieties, such as cycloalkyls, cycloalkenyls, heterocyclyls and heteroaryls. Hydrocarbons that are liquid at standard conditions (ambient temperature (20° C.) and atmospheric pressure) include but are not limited to pentane, hexane, heptane, octane, nonane, decane, and the various isomers thereof (e.g., n-, iso-, sec-, tert-), as well as some carbon-based molecules derivatized by functional groups including atoms other than carbon.

As used herein, "modified hydrocarbon" is employed to describe a molecule containing carbon atoms, hydrogen atoms, and one or more heteroatoms.

As used herein, a "solid" comprises hydrocarbons and/or modified hydrocarbons as provided herein. Generally, a solid exists substantially as a solid at standard conditions (ambient temperature (20° C.) and atmospheric pressure). As provided herein, a solid hydrocarbon and a modified hydrocarbon include those having cyclic moieties, such as cycloalkyls, cycloalkenyls, heterocyclyls and heteroaryls.

As used herein, "alkyl" refers to a straight or branched hydrocarbon chain that includes a fully saturated (no double or triple bonds) hydrocarbon group. The alkyl group may have 1 to 20, or 1 to 40, carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having 1 to 10 carbon atoms. The alkyl group could also be a lower alkyl having 1 to 6 carbon atoms. The alkyl group of the compounds may be designated as "$C_1$-$C_4$ alkyl" or similar designations. By way of example only, "$C_1$-$C_4$ alkyl" indicates that there are one to four carbon atoms in the alkyl chain, i.e., the alkyl chain is selected from methyl, ethyl, propyl, iso-propyl, n-butyl, iso-butyl, see-butyl, and t-butyl. Typical alkyl groups include, but are in no way limited to, methyl, ethyl, propyl, isopropyl, butyl, isobutyl, tertiary butyl, pentyl and hexyl. The alkyl group may be substituted or unsubstituted.

As used herein, "alkenyl" refers to an alkyl group that contains in the straight or branched hydrocarbon chain one or more double bonds. An alkenyl group may be unsubstituted or substituted.

As used herein, "alkynyl" refers to an alkyl group that contains in the straight or branched hydrocarbon chain one or more triple bonds. An alkynyl group may be unsubstituted or substituted.

As used herein, "cycloalkyl" refers to a completely saturated (no double or triple bonds) mono- or multi-cyclic hydrocarbon ring system. When composed of two or more rings, the rings may be joined together in a fused fashion. Cycloalkyl groups can contain 3 to 40 atoms in the ring(s), 3 to 10 atoms in the ring(s) or 3 to 8 atoms in the ring(s). A cycloalkyl group may be unsubstituted or substituted. Typical cycloalkyl groups include, but are in no way limited to, cyclopropyl, cyclobutyl, cyclopentyl, cyclohexyl, cycloheptyl and cyclooctyl.

As used herein, "cycloalkenyl" refers to a mono- or multi-cyclic hydrocarbon ring system that contains one or more double bonds in at least one ring; although, if there is more than one, the double bonds cannot form a fully delocalized pi-electron system throughout all the rings (otherwise the group would be "aryl," as defined herein). When composed of two or more rings, the rings may be connected together in a fused fashion. A cycloalkenyl group may be unsubstituted or substituted.

As used herein, "cycloalkynyl" refers to a mono- or multi-cyclic hydrocarbon ring system that contains one or more triple bonds in at least one ring. If there is more than one triple bond, the triple bonds cannot form a fully delocalized pi-electron system throughout all the rings. When composed of two or more rings, the rings may be joined together in a fused fashion. A cycloalkynyl group may be unsubstituted or substituted.

As used herein, "aryl" refers to a carbocyclic (all carbon) monocyclic or multicyclic aromatic ring system (including fused ring systems where two carbocyclic rings share a chemical bond) that has a fully delocalized pi-electron system throughout all the rings. The number of carbon atoms in an aryl group can vary. For example, the aryl group can be a $C_6$-$C_{14}$ aryl group, a $C_6$-$C_{10}$ aryl group, or a $C_6$ aryl group. Examples of aryl groups include, but are not limited to, benzene, naphthalene and azulene. An aryl group may be substituted or unsubstituted.

As used herein, "aralkyl" and "aryl(alkyl)" refer to an aryl group connected, as a substituent, via a lower alkylene group. The lower alkylene and aryl group of an aralkyl may be substituted or unsubstituted. Examples include but are not limited to benzyl, 2-phenylalkyl, 3-phenylalkyl, and naphthylalkyl.

"Lower alkylene groups" are straight-chained $—CH_2—$ tethering groups, forming bonds to connect molecular fragments via their terminal carbon atoms. Examples include but are not limited to methylene ($—CH_2—$), ethylene ($—CH_2CH_2—$), propylene ($—CH_2CH_2CH_2—$), and butylene ($—CH_2CH_2CH_2CH_2—$). A lower alkylene group can be substituted by replacing one or more hydrogen of the lower alkylene group with a substituent(s) listed under the definition of "substituted."

As used herein, "heteroaryl" refers to a monocyclic or multicyclic aromatic ring system (a ring system with fully delocalized pi-electron system) that contain(s) one or more heteroatoms, that is, an element other than carbon, including but not limited to, nitrogen, oxygen and sulfur. The number of atoms in the ring(s) of a heteroaryl group can vary. For example, the heteroaryl group can contain 3 to 14 atoms in the ring(s), 5 to 10 atoms in the ring(s) or 5 to 6 atoms in the ring(s). Furthermore, the term "heteroaryl" includes fused ring systems where two rings, such as at least one aryl ring and at least one heteroaryl ring, or at least two heteroaryl rings, share at least one chemical bond. Examples of heteroaryl rings include, but are not limited to, those described herein and the following: furan, furazan, thiophene, benzothiophene, phthalazine, pyrrole, oxazole, benzoxazole, 1,2,3-oxadiazole, 1,2,4-oxadiazole, thiazole, 1,2,3-thiadiazole, 1,2,4-thiadiazole, benzothiazole, imidazole, benzimidazole, indole, indazole, pyrazole, benzopyrazole, isoxazole, benzoisoxazole, isothiazole, triazole, benzotriazole, thiadiazole, tetrazole, pyridine, pyridazine, pyrimidine, pyrazine, purine, pteridine, quinoline, isoquinoline, quinazoline, quinoxaline, cinnoline, and triazine. A heteroaryl group itself can, but need not be, substituted.

As used herein, "heterocyclyl" or "heteroalicyclyl" refers to a monocyclic or multicyclic ring system that contain(s) one or more heteroatoms, that is, an element other than carbon, including but not limited to, nitrogen, oxygen and sulfur. The number of atoms in the ring(s) of a heterocyclyl group can vary. For example, the heterocyclyl group can contain 3 to 14 atoms in the ring(s), 5 to 10 atoms in the ring(s) or 5 to 6 atoms in the ring(s). A heterocycle may optionally contain one or more double or triple bonds, but does not include a fully delocalized pi-electron system throughout all its rings so as to constitute a heteroaryl as provided herein. The heteroatom(s) can be any element other than carbon including, but not limited to, oxygen, sulfur, and nitrogen. A heterocyclyl may further contain one or more carbonyl or thiocarbonyl functionalities, so as to make the definition include oxo-systems and thio-systems such as lactams, lactones, cyclic imides, cyclic thioimides and cyclic carbamates. When composed of two or more rings, the rings may be joined together in a fused fashion. A heterocyclyl may include quaternized nitrogen atoms. Examples of such "heterocyclyl" or "heteroalicyclyl" groups include, but are not limited to, those described herein and the following: 1,3-dioxin, 1,3-dioxane, 1,4-dioxane, 1,2-dioxolane, 1,3-dioxolane, 1,4-dioxolane, 1,3-oxathiane, 1,4-oxathiin, 1,3-oxathiolane, 1,3-dithiole, 1,3-dithiolane, 1,4-oxathiane, tetrahydro-1,4-thiazine, 1,3-thiazinane, 2H-1,2-oxazine, maleimide, succinimide, barbituric acid, thiobarbituric acid, dioxopiperazine, hydantoin, dihydrouracil, trioxane, hexahydro-1,3,5-triazine, imidazoline, imidazolidine, isoxazoline, isoxazolidine, oxazoline, oxazolidine, oxazolidinone, thiazoline, thiazolidine, morpholine, oxirane, piperidine N-Oxide, piperidine, piperazine, pyrrolidine, pyrrolidone, pyrrolidione, 4-piperidone, pyrazoline, pyrazolidine, 2-oxopyrrolidine, tetrahydropyran, 4H-pyran, tetrahydrothiopyran, thiamorpholine, thiamorpholine sulfoxide, thiamorpholine sulfone, and their benzo-fused analogs (e.g., benzimidazolidinone, tetrahydroquinoline, and 3,4-methylenedioxyphenyl). A heterocyclyl group itself can, but need not be, substituted.

The various molecules and groups as described herein can be converted or produced or propagated in methods of various embodiments. The words "propagation" as applied to molecular growth of hydrocarbons, modified hydrocarbons, and solid phase hydrocarbons and "converting" a gas to a liquid or solid are also used interchangeably herein.

In a preferred embodiment, a device is provided for propagating molecular growth of hydrocarbons, either straight or branched chain structures, that naturally occur in the gas phase to a molecular size sufficient to shift the natural occurring phase to a liquid or solid state comprises a vessel having an inlet, an outlet and an electrode within the vessel; and a power supply coupled through the vessel to the electrode, which propagates the molecular growth of hydrocarbons. The power supply is coupled to the electrode such that an electric field is induced within the vessel which creates a plasma in the gas within the vessel wherein propagation to the liquid and solid phase can be initiated and maintained. As such, low to moderate pressures within the vessel are maintained, e.g., atmospheric or less to 100 PSIG or more, wherein a preferred range is atmospheric to 5, 10, 15, 25, 50, or 75 PSIG. In addition, it is believed that the electrostatic induced plasma excites electrons in the electron cloud of the gas molecule and minimizes the energy transfer to the nucleus of the gas phase molecules. This hypothesis is supported in that it is has been found that the process causes little, if any, temperature rise in the gas itself or in the liquid downstream of the reaction chamber. Accordingly, the process can be conducted at outdoor ambient temperatures, e.g., −90° C. to 58° C., or higher or lower temperatures, as desired, although temperatures are desirably controlled so as to obtain a desired product in liquid or solid form. Generally, as pressure increases, collisions of molecules and ions will increase. Without wishing to be limited by theory, it is hypothesized that higher pressures may enhance propagation rate, and/or absolute molecular size due to propagation. In some embodiments, pressure may be selected to be sufficient to overcome open line flow resistance. In some embodiments, pressure can be about 200 PSIG, 300 PSIG, 400 PSIG, 500 PSIG, 1000 PSIG, 2500 PSIG, 5000 PSIG, or values there between. In certain embodiments, subjecting to a plasma can be conducted at a pressure from atmospheric pressure to 100 PSIG. In further embodiments, subjecting to a plasma can be conducted at atmospheric pressure.

FIG. 1 is a schematic of a preferred embodiment of the device 100. The device 100 is comprised of an annular reaction chamber or vessel 1 of the type found in oil or gas process, and can be fabricated to comply with the AMSE Code for Pressure Vessels, Section VIII. While an annular reaction chamber can advantageously be employed, other reaction chamber configurations can also be employed in certain embodiments. These can include multi-tube systems, parallel plate systems, honeycomb configurations, cylindrical, spherical, or any other desired configuration. Because the process can advantageously be conducted at lower pressures and temperatures, flexibility in reactor configuration can be achieved. In one embodiment, the vessel is fabricated so as to fit a standard shipping pallet size so as to facilitate transport to remote locations, and additional components of the system can be designed to assemble in a modular fashion on site.

The vessel includes at least one electrode 2, also called a powered electrode herein to refer to an electrode to which an electrical power source is coupled; gas inlet 12, which is coupled on its upstream side to the gas phase feed, which can be sourced from natural gas reserve or another supply (not shown); a liquid outlet 30, which is coupled on its downstream side to the liquid or product collection unit (not shown); and a power supply 8 coupled to the electrode 2. The electrodes employed can be those commercially available for use in plasma generating systems, or can be specifically configured to the reactor and conditions encountered in the process application.

The power supply 8, more fully described below, provides power to the electrode 2 in the form of an application voltage of 1,000 to 100,000 volts alternating current, at a frequency range of 60 to 1,000 Hz, wherein it has been found that voltages of approximately 24.6 KVAC (24,600 VAC) at approximately 440 Hz, and 20,000 VAC at approximately 300 Hz, are preferred. The power supply 8, if it does not supply its own power, is connected to external or operational input power source at the particular site. External power supplies with voltages of 110/115, 208/220/240 or 440 VAC in either, possibly in the form of a 440 volt, single or three phase source supply and frequencies of 50 or 60 Hz as well as other combinations can be utilized. In that event, the power supply takes the external or operational input power and modifies the voltage and frequency as required, as further explained herein. The power supply 8 is coupled to the electrode 2 via a high voltage cable 11, through the reaction vessel entrance 6 and high voltage insulator entrance bushing 4. In a preferred embodiment, the external surface of the reaction chamber 1 is maintained at ground potential, zero voltage, via the reaction chamber ground connection 7. The reaction chamber ground connection 7 is designed to function as a primary ground pathway to ensure elimination of electrical potential on the exterior of the reaction chamber 1. The power supplied to the electrode 2 creates an electric field in the gas region or plasma zone 13, sec FIG. 1 and FIG. 3, located within the vessel 1 between the electrode 2 and the vessel 1, it being understood that the vessel 1 is at ground potential. A secondary ground pathway is provided by the hard piped confirmation to the gas feed source and liquid product outlet, that is, the piping being grounded, for example at 50 and 55, also provides an additional safeguard. In locations where liquid fuel (e.g., diesel fuel), gaseous fuel (e.g., natural gas or propane) or electricity are readily available, these can be employed to provide energy to the power supply, e.g., through the use of diesel or natural gas generators, or solar cell systems. In remote locations, it can be desirable to supply energy to the power supply via combustion of a portion of the gaseous hydrocarbons and to subject a remaining portion of the gaseous hydrocarbons to conversion, or to retain a portion of the liquid hydrocarbons produced to employ as a fuel for a generator. Other apparatus and methods for generating electricity can be employed or adapted to supply energy to the power supply. In some embodiments, device 100 need not operate as an electrically grounded system. In certain embodiments, the electrode 2 and vessel 1 can be maintained at a voltage above ground potential. For example, if a multiphase, such as a 3 phase, power source is employed, it may be advantageous to connect electrode 2 and/or vessel 1, to phases of the power supply 8. In such embodiments, the ground 7 would be replaced by electrical connection to an appropriate phase of power supply 8. In some embodiments, the voltage can be from about 1000 to 100,000 volts, from about 10,000 to 50,000 volts AC, from about 20,000 to 30,000 volts AC, from about 24,000 to 26,000 volts AC. In certain embodiments, field can oscillate at a frequency from 60 to 1000 Hz or from 300 to 600 Hz.

The frequency of the applied voltage may be tuned depending on the size of the vessel 1, the gas feed composition and the targeted product vapor pressure range. Without wishing to be limited by theory, it is believed that the frequency of the applied voltage should be selected to correspond to the capacitance of vessel 1. The capacitance of vessel 1, along with other components of the power circuit, may provide a particular resonance frequency.

The power supply 8 is a unit that is able to provide power of both variable frequency and variable alternating current voltage potential to the electrode 2. The power supplied to the electrode 2 is modified by adjusting the voltage potential or by modifying the frequency thereof or both to create the desired gas to liquid or solid conversion rate and/or liquid component distribution required by the user. The alternating potential change, or variable frequency, is manipulated at the power supply 8 and adjusted to maximize the gas to liquid or solid conversion rates for various inlet feed streams or for various outlet liquid hydrocarbons and/or modified hydrocarbons, and/or solid phase hydrocarbons as further described herein. As such, an alternating current of variable potential and or variable frequency is applied to the electrode 2 through entrance bushing 4 located in the liquid phase or liquid collection region 16 of the vessel 1. The power supply 8 is capable of modifying both the frequency and voltage supplied in response to the conversion process and in this way optimum conversion of specific hydrocarbons may be obtained. In addition as the feed gas molecular structure may not be constant, such that adjustment of frequency or voltage or both supplied to the electrode 2 is beneficial to the propagation of the molecular hydrocarbons of interest. Apparatus for controlling frequency and voltage of energy provided by a power supply are commercially available. Input from sensors within the system, e.g., of liquid level, of temperature, of pressure, of hydrocarbon and/or modified hydrocarbon composition (e.g., IR detectors, gas chromatography, mass spectrometry, conductivity), or the like can be processed by a microprocessor or other computer or computing system and can be employed to adjust frequency and voltage, the flow rate of gaseous components into the reactor, or other operating conditions.

In certain embodiments, a particular wave form of the energy is selected. The wave form may have a significant impact on the reaction kinetics and/or production composition. Suitable wave forms include, but are not limited to, square waves, triangle waves, sawtooth waves, pulsed waves and/or superimposed waves, e.g., a plurality of high frequency waves that collectively form a square or sinusoidal wave, or a combination of the foregoing. In liquid coalescence applications, e.g., coalescence of water, it is observed that a superimposed or multi-component wave form can greatly enhance coalescence rates. Another option for adjusting, e.g., reaction kinetics and/or production composition, in the power cycle is pulsed (off/on) duties. The fragmentation and chain propagation may be enhanced by pulsing the on/off cycles with a preset timing. The on/off cycle may be at a frequency greater than, the same as, or less than a frequency of the supply power. The on cycle frequency may be independent of the on/off cycle. For example, an on/off cycle frequency lower than the high voltage frequency may be employed, e.g., the on/off cycle is established at 100 times per second with the power frequency at 500 Hz. Alternatively, the on/off cycle frequency is higher than the high voltage frequency, e.g., the on/off cycle established at 500 times per second with the high voltage frequency at 350 Hz.

The electrode 2 is preferably covered with an insulating material, e.g., glass or ceramic, with dielectric properties capable of supporting plasma formation and physical properties able to survive the internal conditions of the reactor vessel 1 for commercial use. Quartz was found to be a material suitable for the electrode covering, however, any other suitable material may also be employed. Certain materials, e.g., ceramics, can potentially be catalytic in nature. For example, certain oxide ceramics can act as catalytic surfaces in hydrocarbon reactions. Thermal pyrolysis has utilized various catalytic materials to promote such reactions. Accordingly, the insulating material can be selected for catalytic properties or an absence of catalytic properties, depending upon the intended feedstock and product stream. In various embodiments, the electrode 2 is coated with a material selected from a glass, a ceramic, such as an oxide such as an alumina, beryllia, ceria, or zirconia, a nitride, a boride, a silicide, or a carbide. In some embodiments, a ceramic can be selected from barium titanate, boron oxide, boron nitride, ferrite, lead zirconate titanate, magnesium diboride, porcelain, silicon aluminum oxynitride, silicon carbide, silicon nitride, magnesium silicate, titanium carbide, yttrium barium copper oxide, zinc oxide, or zirconium oxide. A ceramic material can be crystalline or amorphous.

Control of various components of the devices of the embodiments may be distributed at the various components, for example, control of the power supply, specifically the frequency, the voltage, and on or off power can be manipulated at the power supply. In addition, as the gas within the vessel 1 is converted to liquid or solid within the reactor vessel 1, the volume of liquid or solid increases and the volume of gas, the direct correlation to pressure, decreases, the gas inlet feed rate is held equal to the liquid production rate. Accordingly, internal vessel pressure may be controlled by simply controlling the gas feed flow rate, that is, by operation, increasing or decreasing the opening of the flow valve. On site control may advantageously be employed; alternatively, remote control by use of satellite or cellular technology may also be employed.

Numerous controls or combinations of controls may be manipulated by individuals and/or various centralized control systems can be implemented. In this regard, a master control unit or master controller 9, which may be a programmable logic controller, a PC based system or connected into a distributed control system as is known in the art, is coupled to: the vessel pressure indicator 32 via a pressure controller 14 coupled to a gas inlet 12, via a gas feed control valve 15; liquid outlet 30 via a liquid outlet flow measurement device 10; an emergency isolation valve 21 and an emergency isolation valve 22; a safety relief sensor 20 coupled to a safety relief device or pressure relief device 19 attached to the vessel 1 as commonly used in the industry; a liquid level control device 17, coupled to a liquid control valve 18; and to the power supply 8. The master control unit 9 is able to adjust the electrical potential, or the potential change, or frequency or any combination thereof to the electrode 2 to optimize the conversion rate of gas to liquid or solid. It is also feasible to manipulate the parameters to optimize a particular vapor pressure range, or distribution of compounds, in the product as required by the user. The operation of the system is designed to maximize efficiency by allowing the gas to liquid/solid conversion rate to act as the control basis. As the gas is converted to liquid or solid within the reactor, the volume of liquid or solid increases and the volume of gas, the direct correlation to pressure, decreases. Under this scenario, the gas inlet feed rate will be held equal to the liquid or solid formation and/or production rate. In case of excessive pressure rise, for example, pressure approaching the maximum allowable working pressure (MAWP) of the vessel, the pressure relief valve 19 will respond to release the pressure, a high pressure alarm, integrated into the mater controller 9, will activate, the flow sensor will detect the pressure release flow and the master control unit 9 will respond to the flow sensor 20 to close the emergency feed shut off or isolation valve 21 and de-energize the power supply 8. Mass balance is controlled by outlet flow rate and the pressure variable. As such, the interactions between liquid or solid formation and gas conversion can be used to control the internal pressure and flow rate simultaneously. With this basis, the inlet flow rate is dependent on the internal pressure and the outlet product rate can then be used to optimize the conversion rate. That is, the outlet flow rate is measured and the setting of voltage and frequency optimized to maximize the outlet flow rate (highest conversion). The pressure in the vessel will decrease as the gas is converted to the liquid and/or solid phase. The pressure is then maintained in the vessel by allowing more feed gas into the vessel. Therefore, the inlet flow rate is dependent on the pressure while the pressure will decrease directly proportional with the conversion, or the outlet flow rate.

The frequency and secondary voltage can be manipulated by the master control based on the liquid product flow rate, or solid production rate. The product flow meter 10 inputs the liquid outlet rates to the master controller. The frequency and secondary voltage are manipulated by the master controller 9 to optimize the process, such manipulation of the controlled variables in response to other measurements is well understood for example via a fuzzy logic algorithm. It is understood that the frequency and voltage can also be set by the user and not manipulated such that the process proceeds based on mass balance alone.

With regard to the conversion of liquid, referring for example to FIGS. 11A through 11D, the liquid component can be comprised of numerous hydrocarbon species which can contain both straight and branched chain configurations. TABLE 1 represents a component analysis of liquid phase material of an embodiment according to Example 2, below.

Depending upon the nature of the feedstock, sulfur and/or oxygen containing species, modified hydrocarbons as provided herein, may be present in the product stream in addition to hydrocarbon products. Operating parameters may be adjusted to shift production preferentially to selected sulfur and/or oxygen products, e.g., for ease of subsequent removal, or to minimize production of the most detrimental species.

The product stream may contain molecules including any atom or set of atoms, so long as the constituent atoms can be present in the feedstock. In addition to atoms mentioned above, the product stream may include molecules that contain one or more of pnictogens, such as nitrogen, chalcogens, such as oxygen and sulfur, halogens, such as fluorine, chlorine, bromine and iodine, and metals, such as sodium and titanium, or semi-metals, such as boron and silicon. The product stream may include molecules having functional groups including the aforementioned atoms. In various embodiments, molecules in a product stream may include functionalities such as, for example, alcohols, ethers, ketones, aldehydes, carboxylic moieties such as acids and esters, carbonates, sulfides, sulfones, amines, amides, carbamates, nitros, oximes, peroxides, hydrazines, and other functionalities familiar to those of skill in the art.

In some embodiments, a product stream can include a modified hydrocarbon. A modified hydrocarbon as provided herein includes a liquid or solid hydrocarbon in which one or more hydrogen atoms is replaced by a heteroatom. Modified hydrocarbons include those in which a ring is formed by the heteroatom, for example, to constitute a heteroaryl and/or heterocyclyl as provided herein. For example, methylamine is defined as a modified methane, while benzoic acid is defined as a modified toluene. The heteroatom that replaces a hydrogen atom can be any suitable heteroatom provided herein. When including one or more double bonds, a modified hydrocarbon as provided herein is interpreted to include all tautomeric forms.

The product stream can include a liquid or solid hydrocarbon modified with any suitable substituent. For example, a modified hydrocarbon can include one or more of alkoxy, cycloalkyl, cycloalkenyl, acylalkyl, alkoxyalkyl, aminoalkyl, amino acid, aryl, heteroaryl, heterocyclyl, aryl(alkyl), heteroaryl(alkyl), heterocyclyl(alkyl), hydroxy, hydroxyalkyl, acyl, cyano, halogen, thiocarbonyl, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, azido, nitro, silyl, sulfenyl, sulfinyl, sulfonyl, haloalkyl, haloalkoxy, trihalomethanesulfonyl, trihalomethanesulfonamido, amino, mono-substituted amino, di-substituted amino, boronic acid, or ferrocene as those terms are understood by those of skill in the art. Heteroaryl substituents include, but are not limited to imidazoles, furans, thiophenes, pyrroles, pyrimidines, pyrazines, pyridines, pyrazoles, oxazoles, isoxazoles, benzothiophenes, benzofurans, indoles, quinolines, isoquinolines, benzooxazoles, benzoisoxazoles, benzoisothiazoles, benzothiazoles, benzoimidazoles, benzotriazoles, 1H-indazoles, and 2H-indazoles.

The feedstock(s) and mixed component feed materials may be introduced into the reactor at any suitable temperature, e.g., below, at, or above ambient temperature. It can be advantageous to heat the feedstock prior to introducing it into the reaction chamber, so as to ensure that the larger chain hydrocarbons remain in the gas phase as the feedstock enters the plasma zone. The weaker bond strengths of larger chain hydrocarbons may be a driver for carbonyl radical formation that attacks the smaller, stronger bond species. This alternative mode of operation enables shifting the phase of normal state liquids to gas/vapor for homogeneous feed into the reactor. An acceleration in the reaction is also possible by comingling various gas phase hydrocarbons with the primary methane/natural gas source. This co-mingling process may lower the total energy requirement to establish and maintain the fully developed plasma and/or allow product manipulation through co-mingling adjustment. Using higher chain hydrocarbons may increase the ionization and radical formation to drive propagation to components that exist in the liquid or solid phase. In some embodiments, subjecting to a plasma can be conducted at ambient temperature.

To assist the condensation of the propagated hydrocarbon chains, a mechanical device or component in the non-plasma area above or below the plasma reaction zone(s) may be employed. Such a device can be one or more of the types of “demister” materials or apparatus used in conventional liquid/gas separation processes. This configuration can assist in the collection of vapor phase components on the surface to support liquid droplet formation and liquid collection.

Distillation is the process of separating components based on the vapor pressure of the materials. Major petroleum products are categorized into broad groups based on the product take off location, or vapor pressure range, in the distillation process. Products are generally categorized as Light, Middle or Heavy Distillates. Light distillates typically contain hydrocarbons used in gasoline, kerosene and jet fuel. Middle distillates typically contain hydrocarbons used in diesel fuels, heating oil and other light oil applications. Heavy distillates contain hydrocarbons typically used in heavy fuel oils or other heavy oil applications. As such, specific molecular components are not isolated in these valuable products. Therefore, the products resulting from the chain propagation process do not require isolation prior to consumption or additional processing. However, in some embodiments, product stream components may be separated and/or purified as provided herein.

In this regard, the user of the device 100 having a variable frequency power supply 8, may manipulate the liquid/solid component distribution, that is the molecular chains, to be collected, used or otherwise disposed by changing the frequency of the power supplied to the electrode 2. More specifically, by controlling the power to the electrode, varying the frequency or voltage or both, propagation of liquid/solid hydrocarbons of the type, $C_nH_xD_y$, where C is carbon, H is hydrogen and D is another atom, molecule or carbon chain, and n, x and y are the numbers associated with each. Accordingly, various liquid/solid hydrocarbons may be propagated through this process and specific product categories, as defined by their vapor pressure range, may be targeted to be produced as necessary or required.

In some embodiments, a liquid hydrocarbon or a solid hydrocarbon provided herein can have the structure of Formula I:

(I)

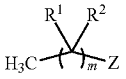

wherein m can be an integer from 0 to 40, each $R^1$ and $R^2$ can independently be hydrogen or a linear, branched, and/or cyclic hydrocarbon moiety of one to twenty carbon atoms, or each $R^1$ and corresponding $R^2$ and the atoms to which they attach can be joined to form a cyclic hydrocarbon moiety of 1 to 8 carbon atoms, and Z can be hydrogen or methyl. In some embodiments, each $R^1$ and $R^2$ may be independently selected from a $C_{1-8}$ alkyl, a $C_{1-8}$ alkenyl, and a $C_{1-8}$ alkynyl. In some embodiments, each $R^1$ and $R^2$ can independently have the structure of Formula (II):

(II)

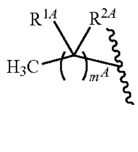

wherein $m^A$ can be an integer from 0 to 8, and each $R^{1A}$ and $R^{2A}$ can independently be chosen from hydrogen, methyl, ethyl, propyl, isopropyl, butyl, isobutyl, sec-butyl, pentyl, 2-methyl butyl, 3-methyl butyl, 2-ethyl propyl, hexyl, 2-methyl pentyl, 3-methyl pentyl, 4-methyl pentyl, heptyl, octyl, nonyl, decyl, undecyl, dodecyl, cyclopropyl, cyclobutyl, cyclopentyl, cyclohexyl, cycloheptyl, cyclooctyl, cyclononyl, and cyclodecyl. Each $R^{1A}$ and $R^{2A}$ can independently be the same or different as any other $R^{1A}$ or $R^{2A}$. Preferably, $m^A$ can be an integer from 0 to 2. Preferably, each $R^{1A}$ and $R^{2A}$ can independently be hydrogen or methyl. Examples of compounds of Formula (I) include, but are not limited, to butane, 2-methyl-butane, 2-methyl-pentane, n-hexane, 2,2,3-trimethyl-butane, 2-methyl-hexane, 2,3-dimethyl-pentane, 3-methyl-hexane, 2,4-dimethyl-hexane, 3,3-dimethyl-hexane, 2,3,3-trimethyl-pentane, 2,3-dimethyl-hexane, 3-methyl-heptane, 2,3,5-trimethyl-hexane, 2,3,3-trimethyl-hexane, 2,3-dimethyl-heptane, 2,2,4-trimethyl-heptane, 2,4,6-trimethyl-heptane, 4-ethyl-2-methyl-hexane, 2,3,5-trimethyl-heptane, 2,3,6-trimethyl-heptane, 2,3,5-trimethyl-heptane, octane, 4-methyl-octane, 3-methyl-octane, 2,4,6-trimethyl-octane, 4,4-dimethyl-octane, 2,5-dimethyl-octane, 2,3,3-trimethyl-octane, 3,4,5,6-tetramethyl-octane, 2,3,6,7-tetramethyl-octane, nonane, 3-methyl-nonane, 4-methyl-nonane, 3-methyl-nonane, decane, 3,6-dimethyl-decane, 2,3,6-trimethyl-decane, 2,5,9-trimethyl-decane, undecane, 2,6-dimethyl-undecane, 5,7-dimethyl-undecane, dodecane, 2,3,3-trimethyl-pentane, 3,3-dimethyl-hexane, 2,3-dimethyl-heptane, 4-methyl-octane, 3-methyl-octane, and 3-methyl-nonane.

In some embodiments, a compound of Formula (I) can be obtained as a mixture with a second, different, compound of Formula (I).

In some embodiments, the second compound is selected from the group consisting of Butane, 2-methyl-Butane, Acetone, Isopropyl Alcohol, 2-methyl-Pentane, n-Hexane, 2,2,3-trimethyl-Butane, 2-methyl-Hexane, 2,3-dimethyl-Pentane, 3-methyl-Hexane, 2,4-dimethyl-Hexane, 3,3-dimethyl-Hexane, 2,3,3-trimethyl-Pentane, 2,3-dimethyl-Hexane, 3-methyl-Heptane, Octane, 2,3,5-trimethyl-Hexane, 2,3,3-trimethyl-Hexane, 2,3-dimethyl-Heptane, 4-methyl-Octane, 3-methyl-Octane, 2,4,6-trimethyl-Octane, 2,2,4-trimethyl-Heptane, 2,4,6-trimethyl-Heptane, Nonane, 4-ethyl-2-methyl-Hexane, 4,4-Dimethyl-octane, 2,3,5-trimethyl-Heptane, 2,5-dimethyl-Octane, 2,3,6-trimethyl-Heptane, 2,3,5-trimethyl-Heptane, 3-methyl-Nonane, 4-methyl-Nonane, 2,3,3-trimethyl-Octane, Decane, 3,4,5,6-tetramethyl-Octane, 3-methyl-Nonane, 3,6-dimethyl-Decane, 2,5,9-trimethyl-Decane, 2,3,6,7-tetramethyl-Octane, Undecane, 2,6-dimethyl-Undecane, 5,7-dimethyl-Undecane, 2,3,6-trimethyl-Decane, and Dodecane.

In some embodiments, a liquid hydrocarbon, solid hydrocarbon, or combination thereof is condensed.

In some embodiments, each $R^1$ and $R^2$ can independently be chosen from hydrogen, methyl, ethyl, propyl, isopropyl, butyl, isobutyl, sec-butyl, pentyl, 2-methyl butyl, 3-methyl butyl, 2-ethyl propyl, hexyl, 2-methyl pentyl, 3-methyl pentyl, 4-methyl pentyl, heptyl, octyl, nonyl, decyl, undecyl, dodecyl, cyclopropyl, cyclobutyl, cyclopentyl, cyclohexyl, cycloheptyl, cyclooctyl, cyclononyl, and cyclodecyl. Each $R^1$ and $R^2$ can independently be the same or different as any other $R^1$ or $R^2$. In some embodiments, m can be an integer from 1 to 20, from 20 to 40, from 1 to 12, from 1 to 8, from 3 to 8, from 3 to 7, from 4 to 7, from 4 to 8, from 5 to 7, or from 5 to 8.

Input to the master controller 9 from the product outlet flow rate via the outlet flow measurement device 10 is a measured dependent variable. The independent variables of potential and frequency are optimized to maximize the conversion rate. The gas feed inlet rate is a dependent variable in direct proportion to the gas to liquid conversion rate that is a direct correlation of the outlet product flow rate. Simply stated, the mass flow rate of the gas feed stream through the inlet 12 is equal to the measured liquid product outlet with a constant vessel pressure.

The high voltage entrance bushing 4 is of the type typically used in high voltage, electrostatic dehydration and desalination processes common to the oil and gas industry. Established oil field equipment companies have successfully utilized high voltage in process applications for many years. In addition, it is noted that the entrance bushing 4 is preferably located in the region of the vessel 1 in which the liquid phase is collected, that is, the liquid phase region or collection area 16. The interface between the liquid and the gas or the liquid level is shown as broken line 5 in FIG. 1.

The liquid level 5, within the liquid phase region 16 is controlled by the liquid level controller 17 that manipulates the liquid control valve 18. The liquid level is maintained for two functions: (1) to create a discrete plasma zone end plane at one end of the reaction chamber 1; and (2) to protect the high voltage entrance bushing 4 from corona attack and deterioration caused by the plasma phase reaction(s). The liquid level 5, and plasma zone interface may be initially established by charging a volume of hydrocarbon liquid, oil or solvent into the vessel 1. This initial charge establishes the liquid-plasma boundary and provides the liquid level protection for the entrance bushing 4.

The safety relief device 19 is located on the reaction chamber 1, above the active plasma reaction zone, to ensure that overpressure scenarios are mitigated, for example, prior to the vessel pressure reaching the maximum allowable working pressure (MAWP) of the reaction chamber 1. In this regard, the emergency relief sensor 20 detects flow through the emergency relief device 19 and signals the master controller 9 which disengages the power supply 8 and closes the reaction chamber gas feed inlet via emergency isolation inlet valve 21 and closes the product outlet via emergency isolation outlet valve 22. In this way, the reaction chamber 1 is de-energized and inlet 12 and outlet 30 are isolated from material flow.

In operation, hydrocarbon gas is fed into the reaction chamber 1 through the reaction chamber gas inlet 12. The reaction chamber gas inlet 12 is located above the gas-liquid interface 5 to maximize retention time in the plasma zone 13 and drive conversion to the liquid or solid phase. The power supplied to the electrode 2 initiates a plasma within the gas in the vessel 1 in plasma zone 13 causing the propagation of the gas to a molecular size sufficient to shift the phase to a liquid or solid. The gas feed rate into the reaction chamber 1 through the reaction chamber inlet 12 is controlled by the reaction chamber pressure controller 14 via the gas feed inlet control valve 15. The reaction chamber pressure controller 14 is coupled to a gas pressure sensor 32. The reaction chamber pressure is maintained within a narrow operating range by allowing gas to flow into the reaction chamber 1 via the feed gas control valve 15 at a mass rate equal to the product outlet rate governed by the conversion from gas to liquid/solid.

Figure 3:
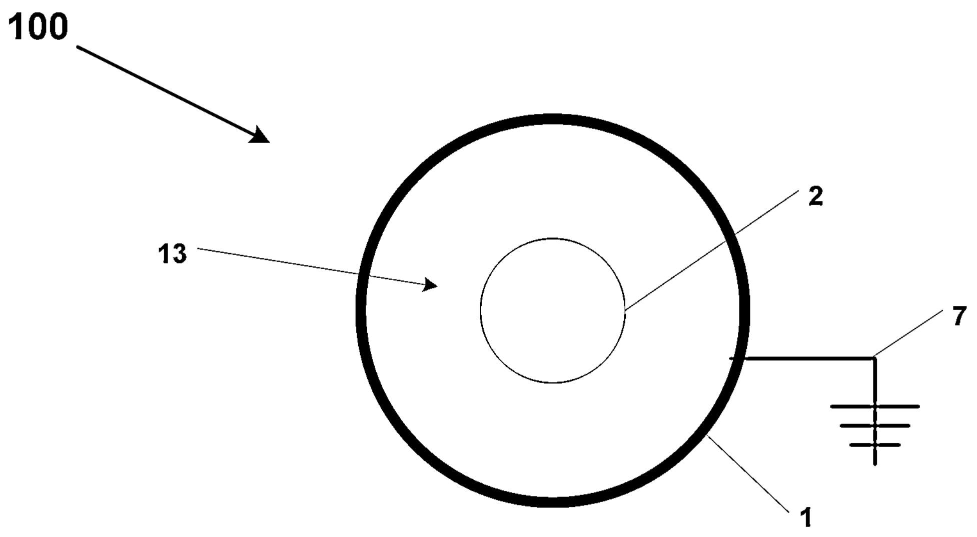
FIG. 3 is a schematic plan view of the vessel 1 and the electrode 2 of FIG. 1.
Figure 4:
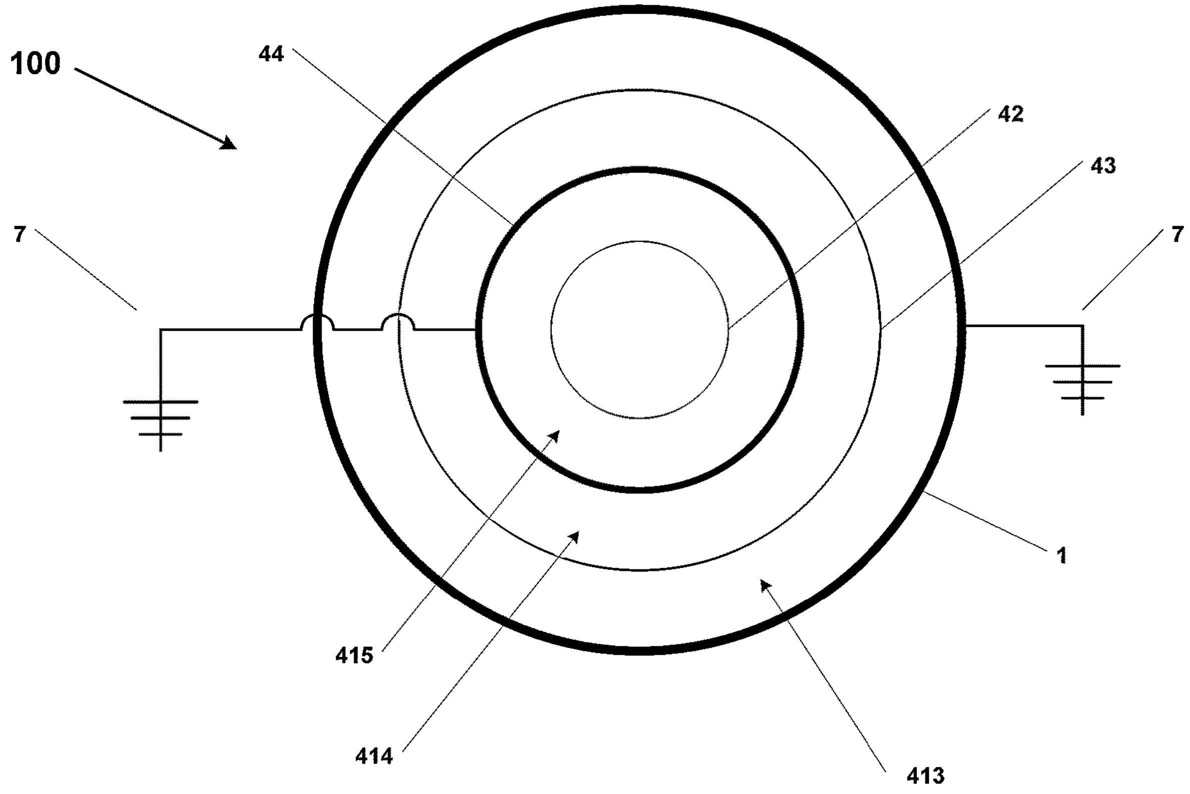
FIG. 4 is a schematic plan view of a vessel 1, as in FIG. 3; however the vessel now includes multiple electrodes 2, 3 and 4.

It is well known that at a particular voltage there is a physical limit to the gap between the electrode and the ground plane to which a plasma zone 13 can be created. This physical restriction in gap size limits the reaction volume of a specific height vessel. One manner to increase the effective reaction volume, while maintaining an effective electrical gradient between the electrode and the ground plane, and without significantly increasing the overall height of the system 100, and without increasing the voltage is to use multiple electrodes. Referring to FIG. 3, the vessel 1, the electrode 2, and plasma zone 13 of FIG. 1 are shown in schematic plan view. Now referring to FIG. 4, the internal plasma reaction volume of the vessel 1 may be increased without increasing the height of the vessel by the addition of one or more powered electrodes and a corresponding one or more grounded electrodes creating additional plasma zones. As shown in FIG. 4, which again is a schematic plan view of the device 100, the vessel 1 includes multiple electrodes 42, 43, and 44. In this embodiment, a further powered electrode 43 is located within the vessel 1 disposed about the powered electrode 42, which corresponds to electrode 2 in FIG. 1 and FIG. 3. In addition, a grounded electrode 44 is disposed about electrode 42 and between electrodes 42 and 43. In this way plasma zone 413, similar to plasma zone 13 of FIG. 1 and FIG. 3, is formed between the electrode 43 and the vessel wall. More importantly, additional plasma zones 414 and 415 are formed between the ground electrode 44 and powered electrode 43 and ground electrode 44 and powered electrode 42 respectively, thereby increasing the total effective reaction volume of the device which thereby increases the gas to liquid/solid conversion rate as compared to the internal volume of the single electrode of the vessel 1 of FIG. 1 and FIG. 3.

Figure 5:
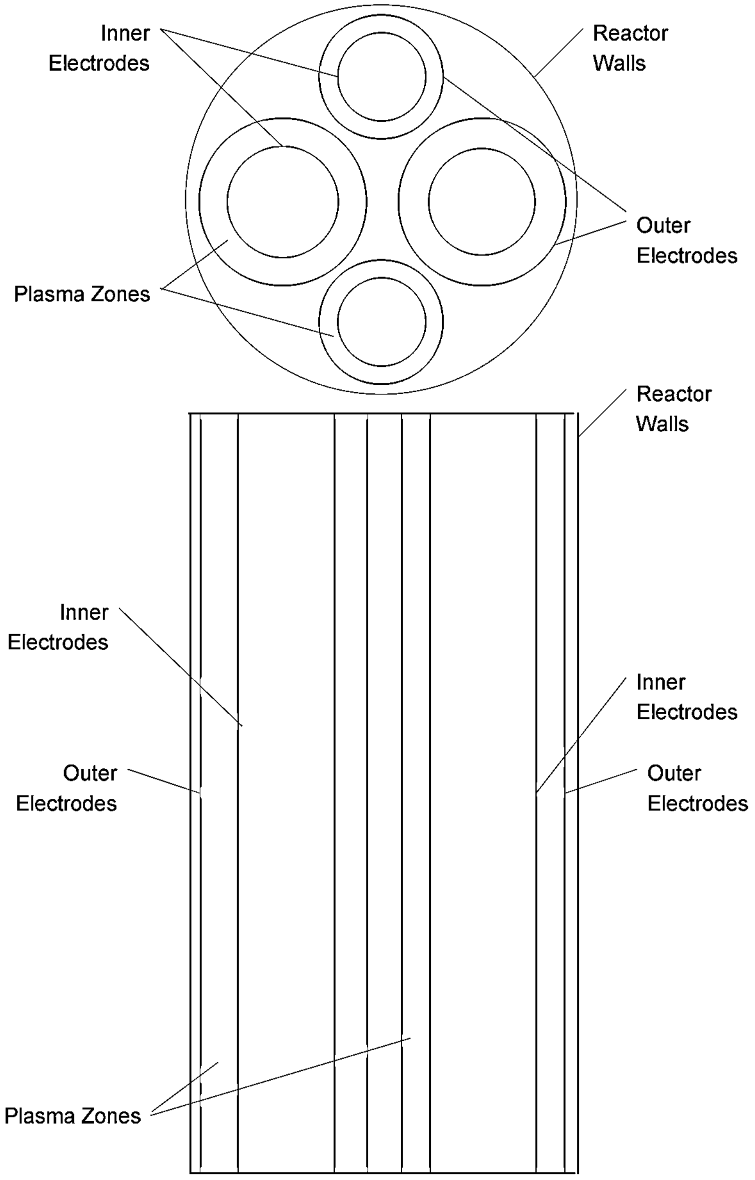
FIG. 5 is a cross section and top view of a reaction vessel having a parallel configuration.
Figure 6:
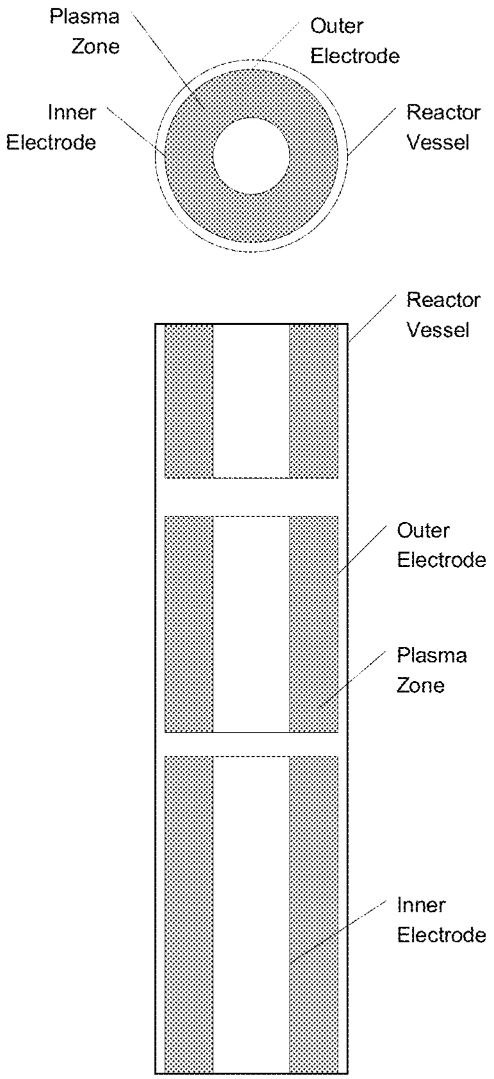
FIG. 6 is a cross section and top view of a reaction vessel having a series configuration.

Various configurations can be employed for the reaction vessel. Parallel configurations (e.g., FIG. 5) enable flow to enter several plasma zones simultaneously. In a series configuration (e.g., FIG. 6), flow passes through sequential plasma zones. Each zone can be the same or different, e.g., having different voltage and/or frequency and/or length. In a longitudinal configuration (e.g., FIG. 7), long, thin plasma zones are formed with free gas gaps between the plasma zones, so as to facilitate free gas to plasma zone interface reactions. In a solid core inner electrode configuration (e.g., FIG. 8), a reactor having a solid core electrode and an insulated outer grounded vessel wall is employed. Such a simple configuration may offer advantages in case of maintenance and/or reduced manufacturing expense.

Figure 7:
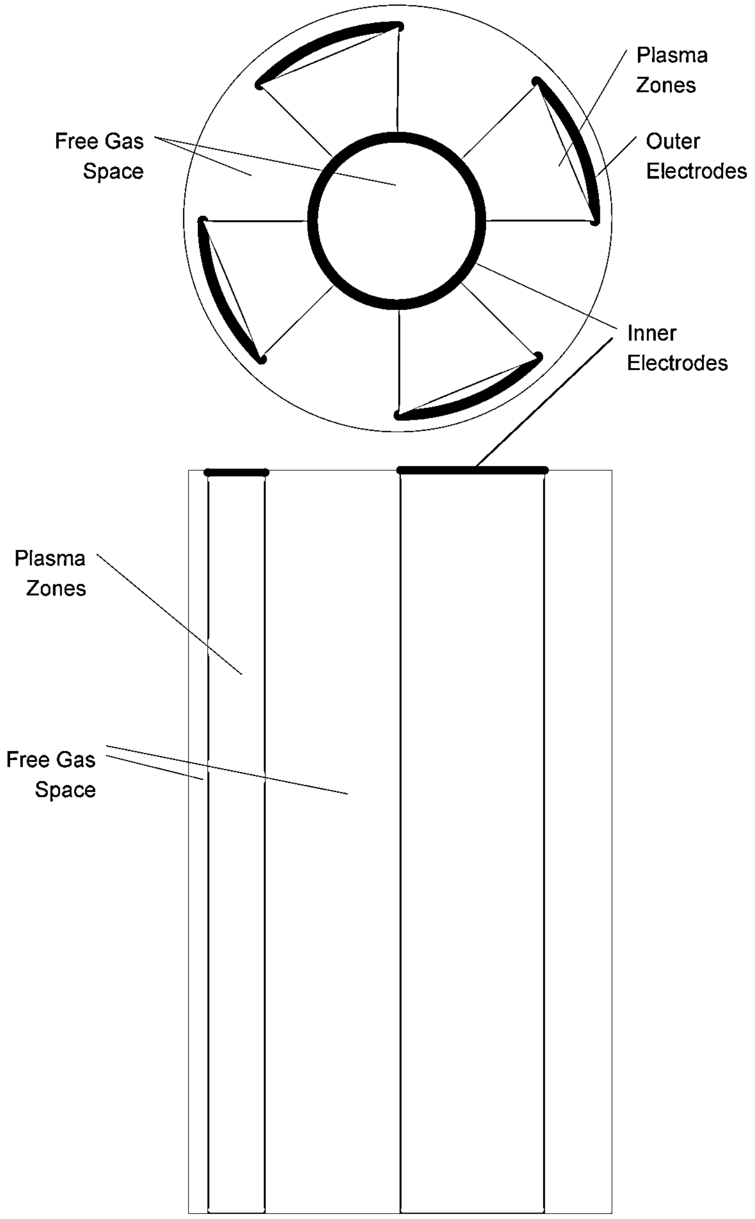
FIG. 7 is a cross section and top view of a reaction vessel having a longitudinal configuration.
Figure 8:
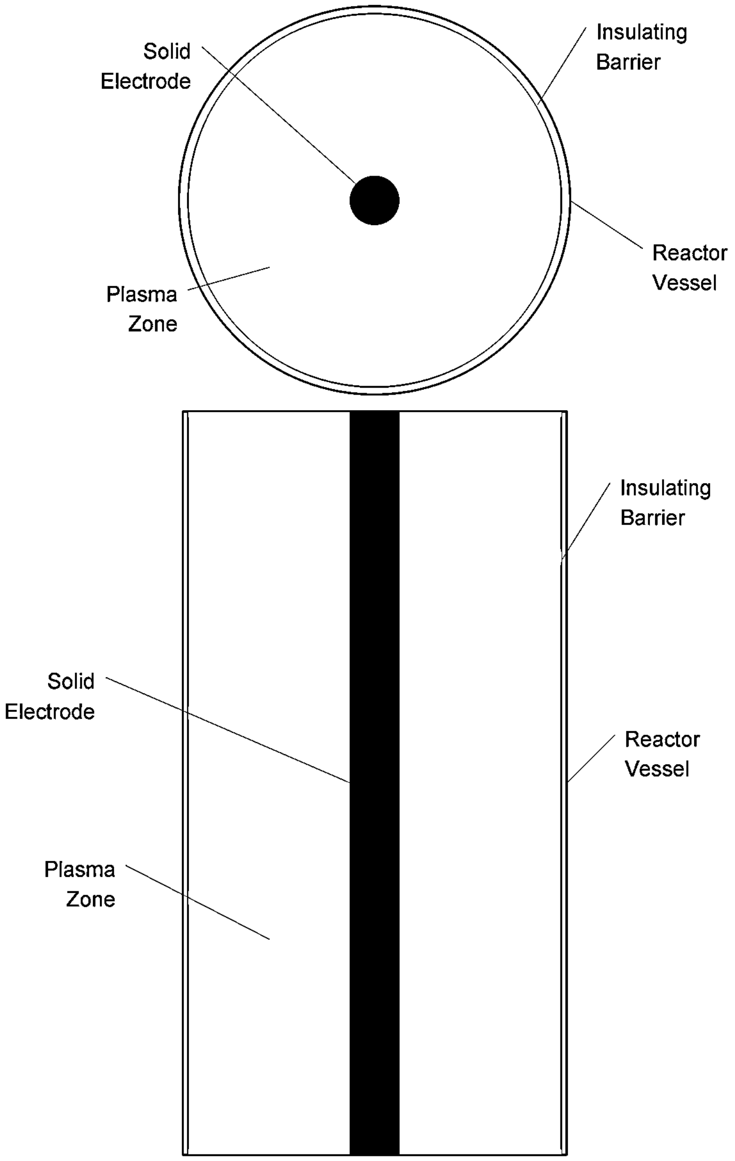
FIG. 8 is a cross section and top view of a reaction vessel having a solid core inner electrode.
Figure 9:
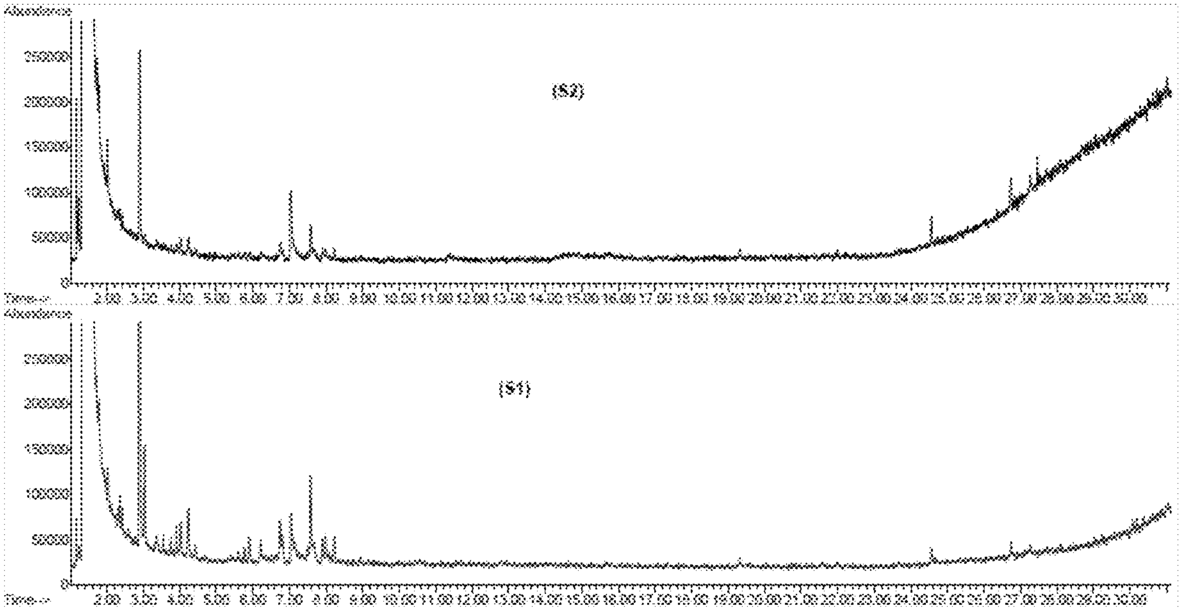
FIG. 9 is a comparison of gas chromatogram of a product stream sample S1 and solid phase sample S2 according to Example 2.
Figure 10:
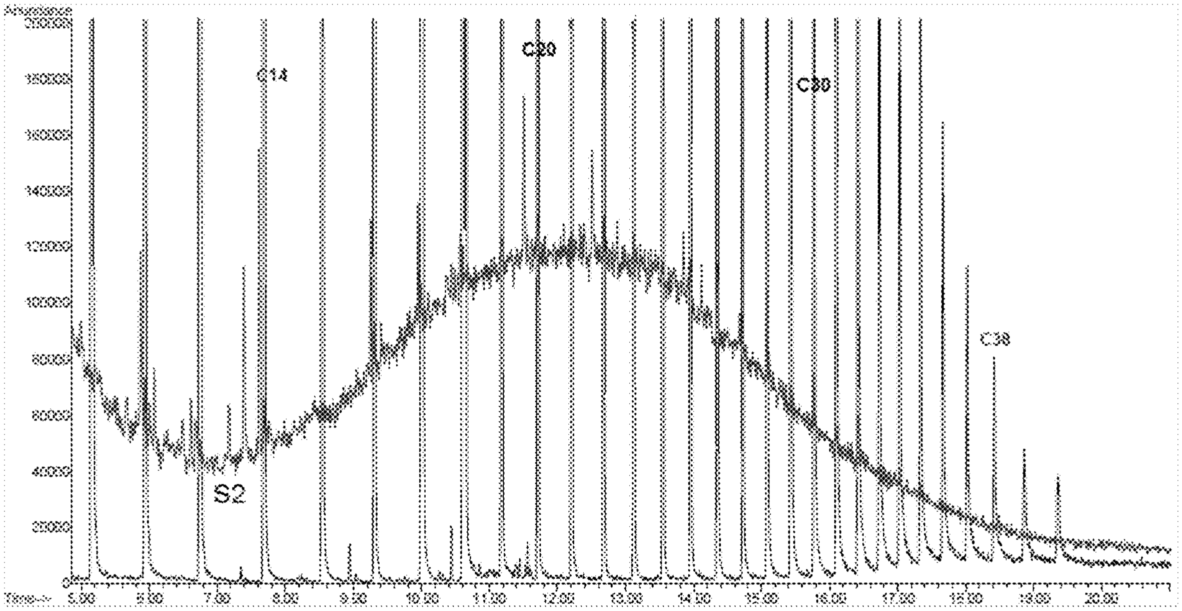
FIG. 10 is a chromatogram according to Example 1 including sample S2 and overlays of various hydrocarbon standards. The chromatogram is shown overlaid with a chromatogram of a sample including straight chain hydrocarbons of increasing chain length as external standards. Each peak on the standard chromatogram represents an additional carbon in the chain.
Figure 11A:
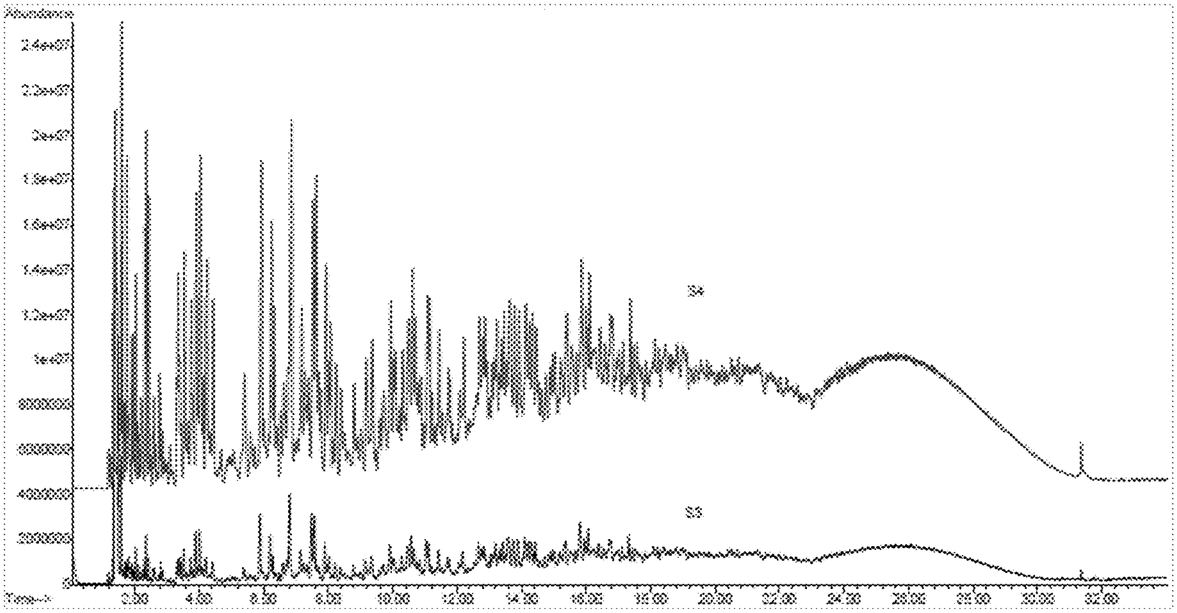
FIGS. 11A to 11D are overlays of gas chromatograms of product stream samples S3 and S4 according to Example 2 acquired under different chromatographic conditions.
Figure 11B:
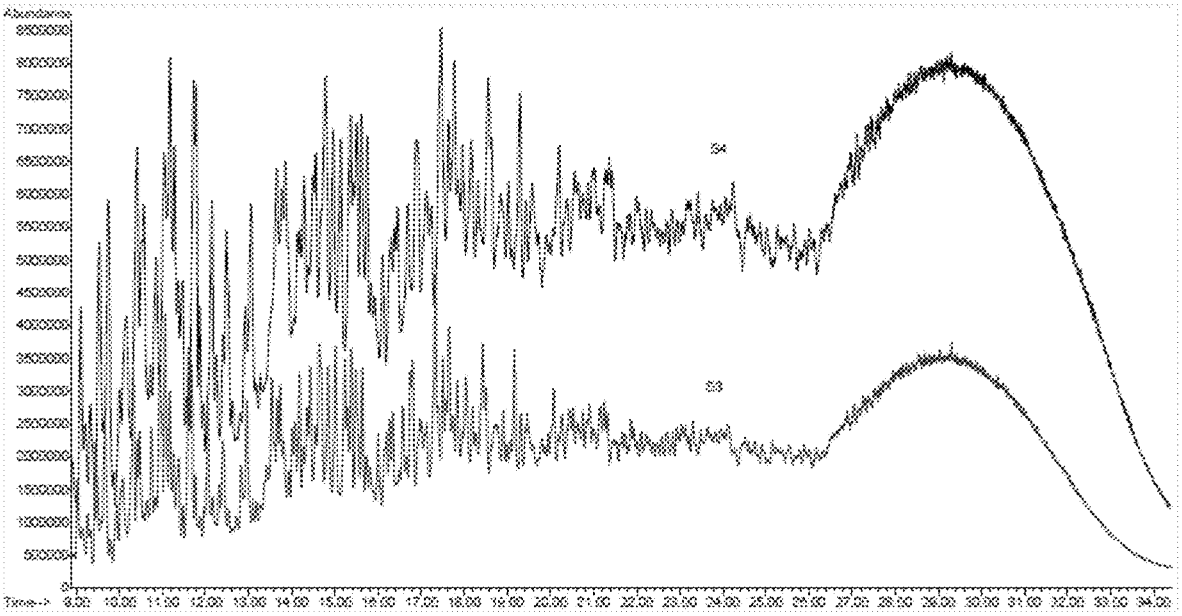
Figure 11C:
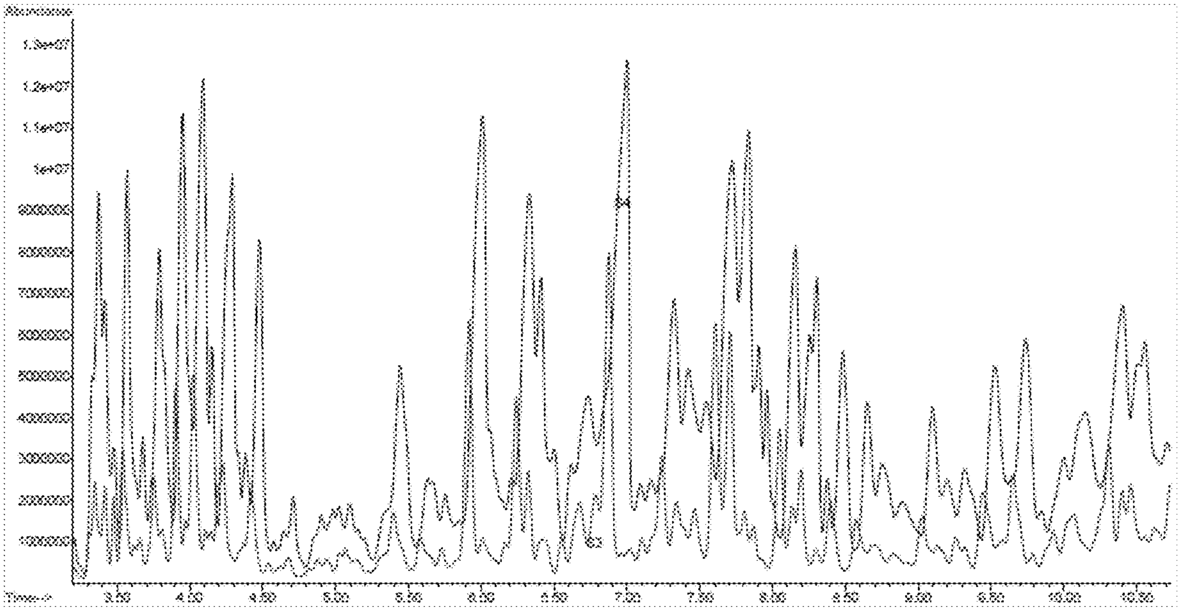
Figure 11D:
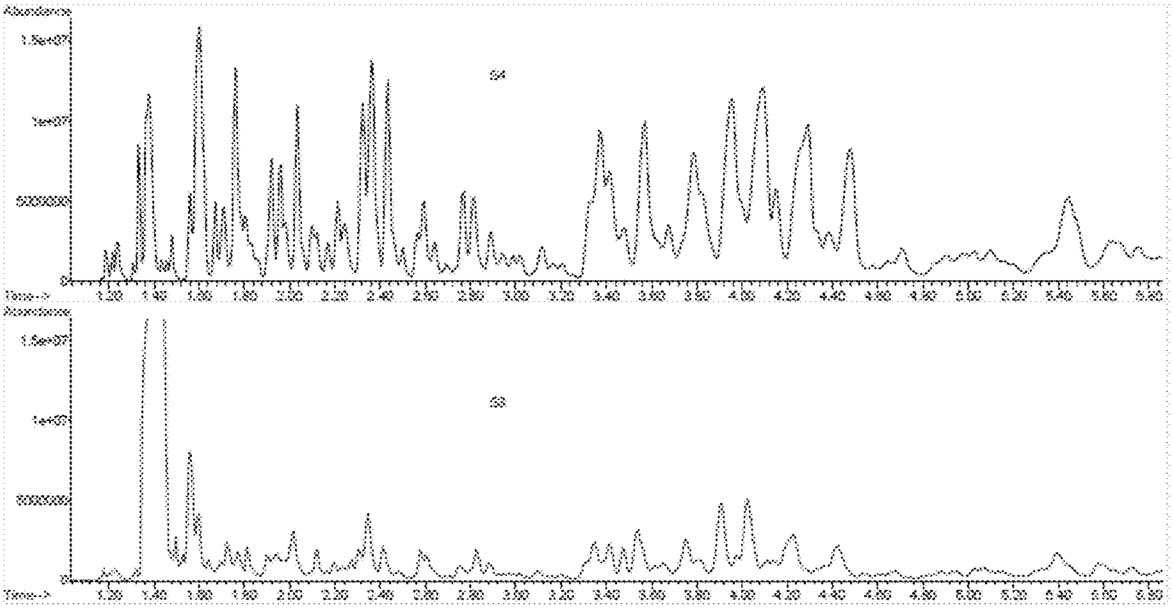
Figure 12A:
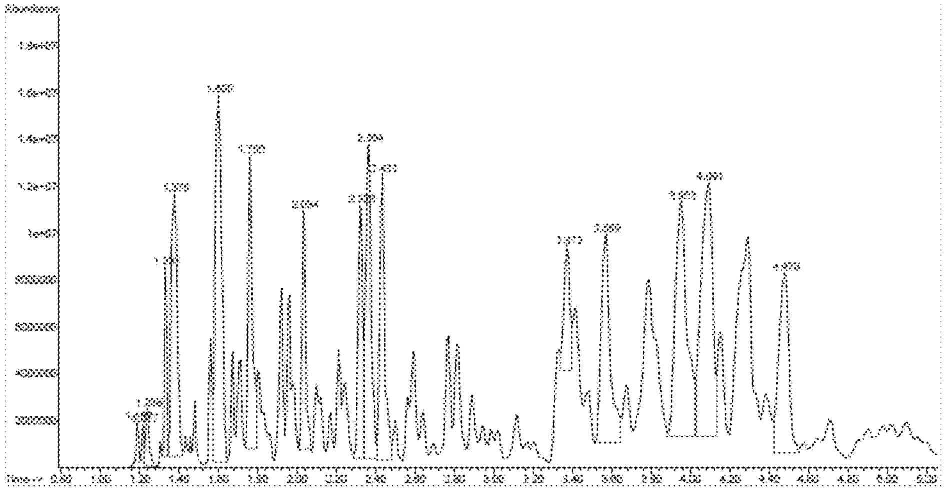
FIGS. 12A to 12C are chromatograms of a product stream sample S4 according to Example 2.
Figure 12B:
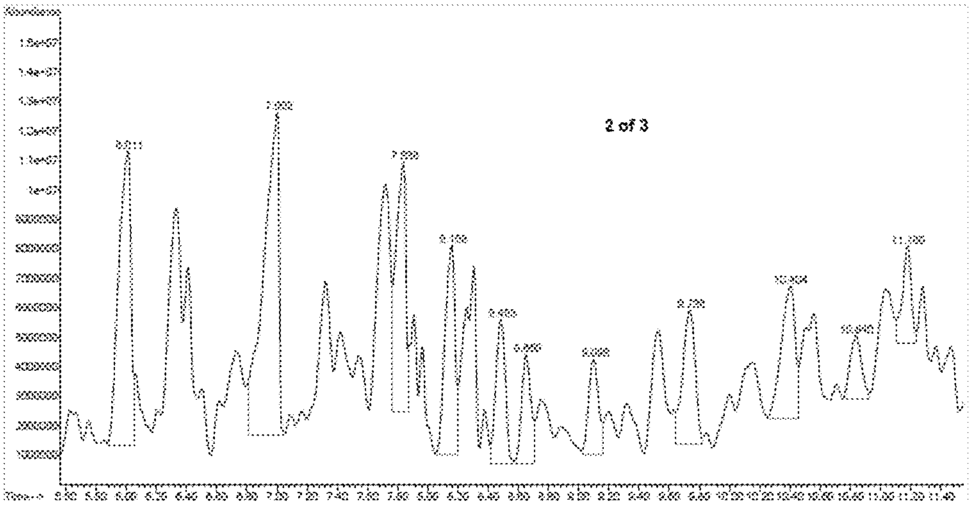
Figure 12C:
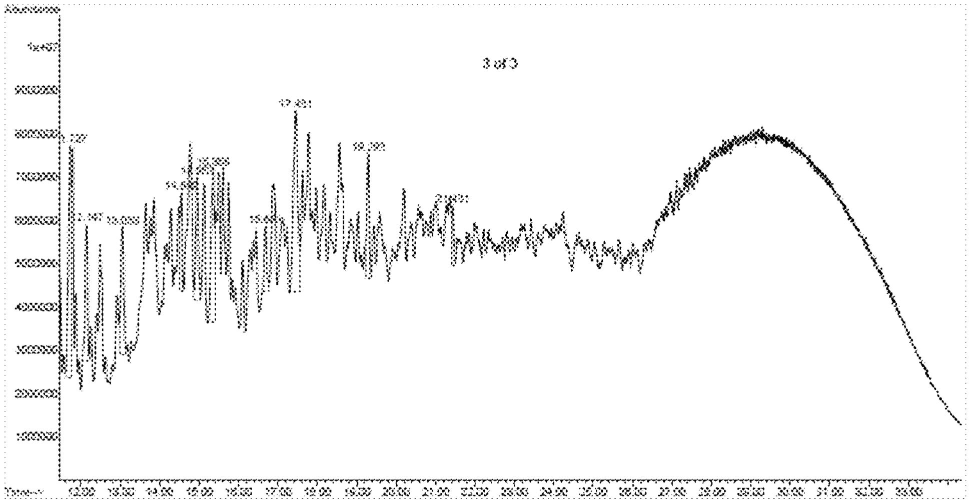
Figure 13:
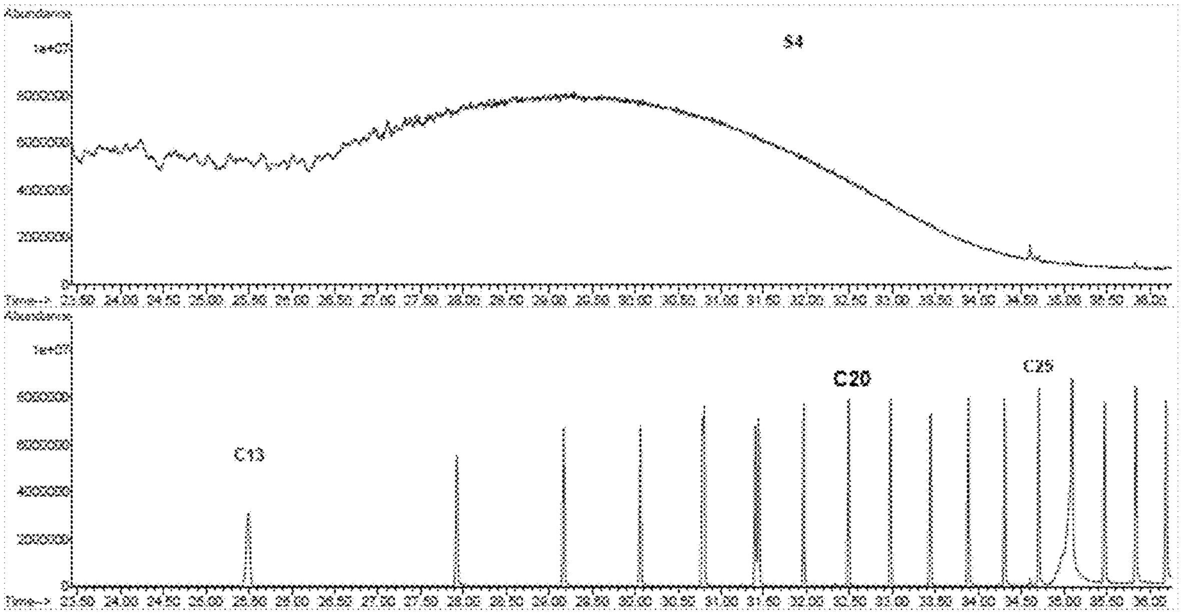
FIG. 13 is a chromatogram of a product stream sample S4 according to Example 1 compared with a chromatogram obtained from a sample of hydrocarbon standards. The standard chromatogram includes straight chain hydrocarbons of increasing chain length as external standards. Each peak on the standard chromatogram represents an additional carbon in the chain, as indicated.

While not wishing to be bound by theory, it is believed that the highest chain propagation may exist at the gas phase/plasma interface and not within the plasma itself. As the hydrocarbon chain increases, the energy level required to fracture the carbon-carbon bonds and/or carbon-hydrogen bonds decreases. Accordingly, as the concentration of higher chain species increases, the reaction would reach an equilibrium of fracturing and recombining of the larger molecules. The energy is readily absorbed in the high chain species and the smaller higher bond energy species become less fractured or form fewer radicals in the equilibrium state. To shift the equilibrium further toward increased propagation rates, a balance of radical formation using the smaller chain species is desired. Accordingly, formation of aggressive radicals that attack non-fragmented molecules is desirable. One example of an interface configuration expected to facilitate this process involves thin plasma zones along the longitudinal direction of the reactor with free gas space between the longitudinal plasma zones, e.g., as depicted in FIG. 7.

Alternatively, the mechanism promoting propagation may be related to the ionized gas, solid material interface that forms along the wetted surface of the plasma zone 13. As such, an embodiment designed to maximize this interfacial area may be employed to enhance propagation rates.

Generally, a product stream produced by the methods or devices provided herein will include a plurality of hydrocarbons and/or modified hydrocarbons. A product stream can include only hydrocarbons, can include only modified hydrocarbons, or can include a mixture of hydrocarbons and modified hydrocarbons. A liquid or solid hydrocarbon or modified hydrocarbon can be any compound prepared by the methods and devices provided herein, for example, those named in Weissermel K. et al., Industrial Organic Chemistry, 3rd, Completely Revised Edition (Wiley, 2008). A liquid or solid hydrocarbon or modified hydrocarbon produced by the methods or devices provided herein may have the structure of Formula (I), as provided herein. Such compounds may be selected from, but are not limited to, those provided in Table 1.

TABLE 1

| IUPAC Chemical Name | Chemical Formula |
|---|---|
| Propane | C3H8 |
| Isobutane | C4H10 |
| Butane | C4H10 |
| Butane, 2-methyl- | C5H12 |
| Acetone | C3H6O |
| Isopropyl Alcohol | C3H8O |
| Pentane, 2-methyl- | C6H14 |
| n-Hexane | C6H14 |
| Butane, 2,2,3-trimethyl- | C7H16 |
| Hexane, 2-methyl- | C7H16 |
| Pentane, 2,3-dimethyl- | C7H16 |
| Hexane, 3-methyl- | C7H16 |
| Hexane, 2,4-dimethyl- | C8H18 |
| Hexane, 3,3-dimethyl- | C8H18 |
| Pentane, 2,3,3-trimethyl- | C8H18 |
| Hexane, 2,3-dimethyl- | C8H18 |
| Heptane, 3-methyl- | C8H18 |
| Octane | C8H18 |
| Hexane, 2,3,5-trimethyl- | C9H20 |
| Hexane, 2,3,3-trimethyl- | C9H20 |
| Heptane, 2,3-dimethyl- | C9H20 |
| Octane, 4-methyl- | C9H20 |
| Octane, 3-methyl- | C9H20 |
| Octane, 2,4,6-trimethyl- | C11H24 |
| Heptane, 2,2,4-trimethyl- | C10H22 |
| Heptane, 2,4,6-trimethyl- | C10H22 |
| Nonane | C9H20 |
| Hexane, 4-ethyl-2-methyl- | C9H20 |
| 4,4-Dimethyl octane | C10H22 |
| Heptane, 2,3,5-trimethyl- | C10H22 |
| Octane, 2,5-dimethyl- | C10H22 |
| Heptane, 2,3,6-trimethyl | C10H22 |
| Heptane, 2,3,5-trimethyl- | C10H22 |
| Nonane, 3-methyl- | C10H22 |
| Nonane, 4-methyl | C11H24 |
| Octane, 2,3,3-trimethyl- | C11H24 |
| Decane | C10H22 |
| Octane, 3,4,5,6-tetramethyl- | C12H26 |
| Nonane, 3-methyl- | C10H22 |
| Decane, 3,6-dimethyl- | C12H26 |
| Decane, 2,5,9-trimethyl- | C13H28 |
| Octane, 2,3,6,7-tetramethyl- | C12H26 |
| Undecane | C11H24 |
| Undecane, 2,6-dimethyl- | C13H28 |
| Undecane, 5,7-dimethyl- | C13H28 |
| Decane, 2,3,6-trimethyl- | C13H28 |
| Dodecane | C12H26 |

In certain embodiments, a liquid or solid hydrocarbon or modified hydrocarbon as provided herein may be characterized by its degree of unsaturation. For example, a liquid or solid hydrocarbon or modified hydrocarbon can have one degree of unsaturation, two degrees of unsaturation, three degrees of unsaturation, four degrees of unsaturation, five degrees of unsaturation, or more. In other embodiments, a liquid or solid hydrocarbon or modified hydrocarbon as provided herein can be characterized by the included number of rings. For example, a liquid or solid hydrocarbon or modified hydrocarbon can include no rings, one ring, two rings, three rings, four rings, five rings, or more.

Liquid and/or solid hydrocarbons and/or modified hydrocarbons synthesized by the methods and devices provided herein are useful for many purposes. The liquid and/or solid hydrocarbon and/or modified hydrocarbon can be an isolated material or a mixture of materials. A liquid and/or solid hydrocarbon and/or modified hydrocarbon provided herein may be suitable for purposes including, but not limited to fuels, adhesives, construction materials, chemical treatments, solvents, coatings, building blocks for chemical synthesis, preservatives, pharmaceuticals, personal care products, and refrigerants. A liquid and/or solid hydrocarbon and/or modified hydrocarbon provided herein may be useful for polymerization to create materials useful as fabrics, packaging, furnishings, leisure devices including but not limited to toys, home maintenance and improvement technologies such as hoses, lawn figurines, wall ornaments, fire extinguishers, HVAC equipment and control devices, lighting, electrical infrastructure, clotheswashing and dishwashing equipment, flooring materials including padding, insulation, devices for cooking, and appliances.

It may be desirable to separate certain product stream materials from other product stream materials. Any suitable method or methods of separation can be used. Persons of skill in the art have a number of methods and devices available to separate such materials. Numerous types of chemical, physiochemical, and physical separation methods are known to those of skill in the art, for example, including fractional distillation, affinity chromatography including, for example, centrifugal chromatography, thin-layer chromatography, gas chromatography and high pressure liquid chromatography; crystallization; electrophoresis; osmotic pressure-driven methods; and methods relying on disparate solubility including, for example, solvent extraction, and trituration. Separation techniques known to persons of skill in the art include adsorption, capillary electrophoresis, centrifugation, cyclonic separation, chromatography, countercurrent membrane separation, crystallization, decantation, demister (vapor), distillation, drying, electrophoresis, elutriation, evaporation, extraction (for example, liquid-liquid extraction), leaching, field flow fractionation, flotation, flocculation, filtration, fractional freezing, gravimetric separation, precipitation, scrubbing, sedimentation, stripping, and sublimation. See, for example, Budhiraja, R. P., Separation Chemistry (New Age International Ltd, 2010). Distillation devices are described in, for example, U.S. Pat. Nos. 5,271,810, 5,045,155, 4,234,391, and 9,194,623. Chromatographic separation devices are described in, for example, U.S. 2007/0163960, U.S. 2008/0164193, U.S. 2011/0232373, U.S. Pat. Nos. 3,954,608, 4,139,458, and 4,678,570.

Separation of a plurality of product stream materials can be by fractional distillation according to the knowledge of persons of skill in the art. Fractional distillation separates chemical compounds boiling point by heating them to a temperature at which one or more fractions of the compound will vaporize. Compounds can be separated because a compound will be in the vapor phase only above its boiling temperature (at the pressure in the column). Fractional distillation utilizes a fractionating column. A fractionating column includes nodules upon which condensation and reboiling can occur. Cycles of condensation and boiling allow each component to reach equilibrium, such that only compounds having a boiling point above the temperature of the mixture will remain in the vapor phase and reach the top of the column. Compounds in the vapor phase that reach the top of the fractionating column are condensed and thus separated from the other components of the mixture. As understood by persons of skill in the art, compounds with very close boiling points can be separated using fractional distillation provided that a fractionating column of sufficient length is used. Simple distillation can also be used to separate compounds having substantially different boiling points. A simple distillation column generally includes a smooth inner surface which is generally cylindrical in the interior dimension, although other shapes may be used. The separation efficiency can be determined by the number of theoretical plates. The Fenske equation provides a method for determining the number of theoretical plates needed for separation, for example, of two components:

$$N = \frac{\log\left[\left(\frac{X_d}{1 - X_d}\right)\left(\frac{1 - X_b}{X_b}\right)\right]}{\log\alpha_{avg}}$$

Where: $\alpha_{avg}$ is the average relative volatility of the more volatile component to the less volatile component; $X_d$ is the mole fraction of more volatile component in the overhead distillate; $X_b$ is the mole fraction of the more volatile component in the bottoms liquid; and N is the minimum number of theoretical plates or trays required at total reflux. Distillation can be implemented as a batch distillation or continuous distillation.

Chemical derivatization, such as salt formation, esterification, or etherification of one or more species present in a mixture may be performed in conjunction with one or more of the foregoing methods.

A separation can be used to obtain an isolated hydrocarbon or modified hydrocarbon as provided herein. An isolated hydrocarbon can include one or more structural isomers. An isolated hydrocarbon can be characterized by a range of molecular weight, by a degree of branching, or by a degree of unsaturation, physical characteristic such as boiling point, degree of unsaturation, degree of branching or a functional group present in each member of the class, for example, alcohols, amides, carboxylic acids, olefins, and/or alkynes. In some embodiments, an isolated liquid hydrocarbon can be characterized by a range of boiling points.

In some embodiments, liquid and/or solid hydrocarbons in the product stream can be separated into individual compounds. Such separation can be accomplished by any method provided herein, or known to persons of skill in the art.

A compound produced by the methods and devices provided herein can be purified by any suitable method. Numerous types of purification methods are known to those of skill in the art, for example, including distillation, chromatography such as gas chromatography, crystallization, electrophoresis, osmotic pressure-driven methods and methods relying on disparate solubility. Chemical derivatization of the species to be purified, or an impurity accompanying such a species, may be performed in conjunction with one or more of the foregoing methods. For purification methods, see, for example, W. L. F. Armarego et al., Purification of Laboratory Chemicals, (Butterworth-Heinemann, 2012).

In some embodiments, a compound is purified by gas chromatography. Persons of skill in the art possess the knowledge and resources to conduct gas chromatography. Generally, gas chromatography includes the steps of vaporizing a sample by applying heat and/or vacuum, and passing the vaporized sample through a column. A column can be a tube containing a stationary phase, or packing, of liquid or polymer on an inert solid support. A gas chromatography column will generally include a stationary phase comprising a material selected to interact with components of the vaporized sample. Due to disparate affinity of each component with the packing, each component has a different retention time in the column. For a study on the separation of hydrocarbons by gas chromatography, see for example, Singh, B. N., et al., Separation of light hydrocarbons by gas chromatography using serpentine as stationary phase, Indian J. of Chem. Tech. (November 2004), Vol. 11, pp. 793-796, which is incorporated herein by reference in the entirety.

In some embodiments, a liquid and/or solid hydrocarbon or modified hydrocarbon synthesized by a method or device provided herein can be subjected to a plurality of isolation and/or purification procedures provided herein and/or known to those of skill in the art. For example, a liquid hydrocarbon can be isolated by distillation, and subsequently purified by gas chromatography to provide a substantially pure compound provided herein, such as a compound of Formula (I), where substantially pure means that the compound is free from gas-chromatography detectable impurities. The compound can also be a purified compound, wherein a mixture containing the compound is subjected to steps to remove extraneous compounds to yield an enriched product containing at least 70%, 80%, 90%, 95%, 98%, 99%, 99.5%, or 99.9% of the compound.

Example 1

Figure 2A:
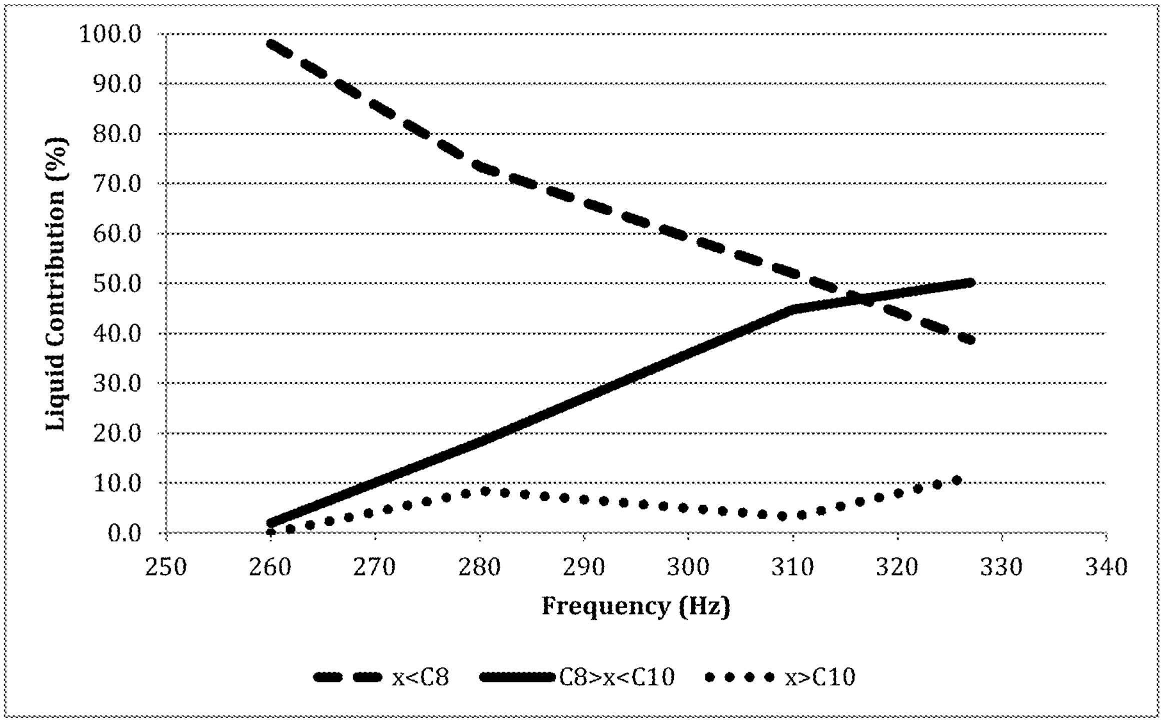
FIG. 2A is a graph showing the effect on liquid contribution of various power supply frequencies applied to the electrode in an embodiment according to Example 1.
Figure 2B:
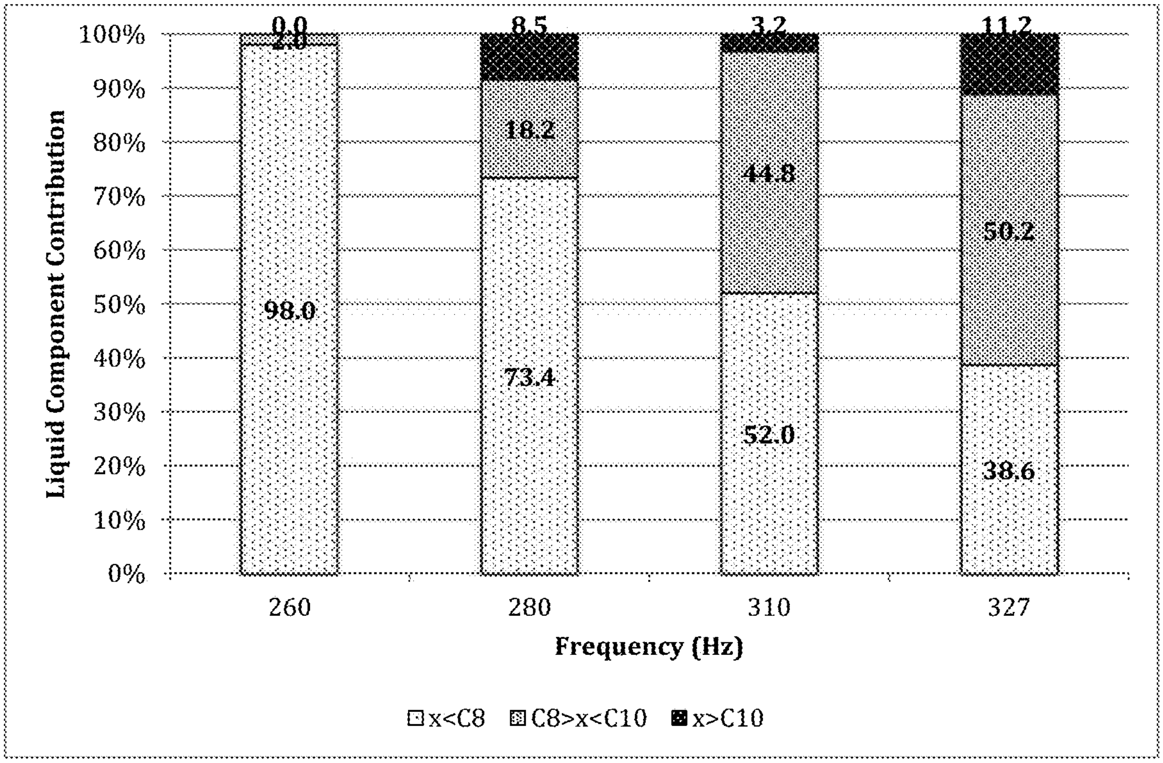
FIG. 2B is a graph showing the effect on liquid component contribution of various power supply frequencies applied to the electrode in an embodiment according to Example 1.

Power supply frequencies applied to the electrode of device 100 were varied using propane as the gas phase hydrocarbon, to produce liquid hydrocarbons and solid hydrocarbons, as indicated in FIGS. 2A and 2B. With regard to the conversion to liquid, referring to FIG. 2B, it is shown that various percentages of different liquid molecules are formed from the hydrocarbon gas at discrete electrical frequencies supplied to the electrode 2. More specifically, FIG. 2B shows the data as obtained from gas chromatography (GC) and shows that the 100%<C8 indicates that most of the liquid species in this group will be recognized on the GC before the C8 standard would be detected. Likewise for the <C10 and >C10. The material being detected between C8 and C10 are not necessarily a specific hydrocarbon, but are chemicals that are detected by the GC after the C8 standard and before the C10 standard. Materials>C10 are species that pass through the GC and are detected after the C10 standard. Thus, there may be some C6, or other chain length, molecules, but the molecular arrangement gives them a vapor pressure higher than the C10 standard. There are possibly hundreds of molecular species that can be formed which will fall into the various groups. It should be noted that at each applied frequency, the total percentage of the converted liquid sums to approximately 100%.

Example 2

A device of FIGS. 1 and 3-8 and as provided herein was operated at the following parameters: 440 Hz; 24,600 VAC sec voltage; atmospheric pressure; and ambient temperature. The gas phase hydrocarbon input was propane.

Four (4) samples were collected. Sample 1 was a solvent blank containing only acetone. Sample 2 was solid residue collected from the reactor wall, diluted. Sample 3 was liquid product stream, diluted. Sample 4 was neat liquid product stream. Descriptions of samples S1 to S4 are provided in Table 2.

Gas chromatography was performed using an Agilent™ HP-5 column, having a 30 m length, a 0.25 mm inner diameter and a split ratio of 50:1. The temperature program was as follows: temperature was held at 40° C. for 3 min; 40-200° C. at a heating rate of 5° C./min; then 200-280° C. at a heating rate of 10° C./min. Mass spectrometry results for sample S4, using a best fit model, are provided in Table 3. Gas chromatography results for sample S4 are provided in Table 4.

TABLE 2

| Sample # | Description |
|---|---|
| S1 | Acetone blank |
| S2 | Solids residue from reactor walls, diluted in acetone |
| S3 | Liquid product stream, diluted in acetone |
| S4 | Liquid product stream, neat |

TABLE 3

| Retention Time (min) | Spectral Match | Mass/ Formula | Match Factor | Reverse Match Factor | NIST Prob. |
|---|---|---|---|---|---|
| 1.185 | Propane | C3H8 | 973 | 973 | 95% |
| 1.217 | Isobutane | C4H10 | 927 | 927 | 80% |
| 1.241 | Butane | C4H10 | 886 | 886 | 73% |
| 1.329 | Butane, 2-methyl- | C5H12 | 956 | 959 | 89% |
| 1.369 | Acetone | C3H6O | 865 | 865 | 61% |
| 1.377 | Isopropyl Alcohol | C3H8O | 720 | 767 | 17% |
| 1.602 | Pentane, 2-methyl- | C6H14 | 916 | 925 | 62% |
| 1.762 | n-Hexane | C6H14 | 925 | 933 | 73% |
| 2.034 | Butane, 2,2,3-trimethyl- | C7H16 | 914 | 914 | 45% |
| 2.322 | Hexane, 2-methyl- | C7H16 | 887 | 901 | 48% |

TABLE 3-continued

| Retention Time (min) | Spectral Match | Mass/ Formula | Match Factor | Reverse Match Factor | NIST Prob. |
|---|---|---|---|---|---|
| 2.362 | Pentane, 2,3-dimethyl- | C7H16 | 910 | 910 | 47% |
| 2.435 | Hexane, 3-methyl- | C7H16 | 949 | 949 | 62% |
| 3.372 | Hexane, 2,4-dimethyl- | C8H18 | 926 | 926 | 41% |
| 3.572 | Hexane, 3,3-dimethyl- | C8H18 | 914 | 915 | 38% |
| 3.956 | Pentane, 2,3,3-trimethyl- | C8H18 | 914 | 915 | 53% |
| 4.092 | Hexane, 2,3-dimethyl- | C8H18 | 920 | 922 | 48% |
| 4.478 | Heptane, 3-methyl- | C8H18 | 949 | 957 | 42% |
| 5.41 | Octane | C8H18 | | | |
| 6.015 | Hexane, 2,3,5-trimethyl- | C9H20 | 937 | 938 | 42% |
| 7.000 | Hexane, 2,3,3-trimethyl- | C9H20 | 890 | 895 | 16% |
| 7.833 | Heptane, 2,3-dimethyl- | C9H20 | 863 | 865 | 29% |
| 8.161 | Octane, 4-methyl- | C9H20 | 902 | 905 | 36% |
| 8.481 | Octane, 3-methyl- | C9H20 | 855 | 874 | 11% |
| 8.649 | Heptane, 2,2,4-trimethyl- | C10H22 | 884 | 916 | 36% |
| 9.090 | Heptane, 2,4,6-trimethyl- | C10H22 | 845 | 859 | 8% |
| 9.710 | Nonane | C9H20 | | | |
| 9.739 | 4,4-Dimethyl octane | C10H22 | 874 | 877 | 22% |
| 10.403 | Heptane, 2,3,5-trimethyl- | C10H22 | 857 | 885 | 32% |
| 10.836 | Octane, 2,5-dimethyl- | C10H22 | 856 | 857 | 21% |
| 11.18 | Heptane, 2,3,6-trimethyl | C10H22 | 853 | 855 | 7% |
| 11.717 | Heptane, 2,3,5-trimethyl- | C10H22 | 842 | 863 | 17% |
| 12.149 | Nonane, 4-methyl | C11H24 | 870 | 881 | 9% |
| 13.054 | Octane, 2,3,3-trimethyl- | C11H24 | 862 | 889 | 13% |
| 14.09 | Decane | C10H22 | | | |
| 14.552 | Octane, 3,4,5,6-tetramethyl- | C12H26 | 835 | 857 | 14% |
| 14.952 | Nonane, 3-methyl- | C10H22 | 842 | 878 | 10% |
| 15.361 | Decane, 3,6-dimethyl- | C12H26 | 848 | 856 | 12% |
| 16.674 | Decane, 2,5,9-trimethyl- | C13H28 | 794 | 844 | 6% |
| 17.451 | Octane, 2,3,6,7-tetramethyl- | C12H26 | 838 | 872 | 11% |
| 18.18 | Undecane | C11H24 | | | |
| 19.293 | Undecane, 5,7-dimethyl- | C13H28 | 872 | 882 | 27% |
| 21.440 | Decane, 2,3,6-trimethyl- | C13H28 | 801 | 844 | 8% |
| 21.970 | Dodecane | C2H26 | | | |

TABLE 4

| Retention Time (min) | Spectral Match | Mass/Formula | Area | Percent |
|---|---|---|---|---|
| 1.185 | Propane | C3H8 | 13674744 | 0.17% |
| 1.217 | Isobutane | C4H10 | 14037704 | 0.17% |
| 1.241 | Butane | C4H10 | 28137338 | 0.35% |
| 1.329 | Butane, 2-methyl- | C5H12 | 70973367 | 0.88% |
| 1.369 | Acetone | C3H6O | 240687131 | 2.97% |
| 1.377 | Isopropyl Alcohol | C3H8O | 360127348 | 4.44% |
| 1.602 | Pentane, 2-methyl- | C6H14 | 200729040 | 2.47% |
| 1.762 | n-Hexane | C6H14 | 132909430 | 1.64% |
| 2.034 | Butane, 2,2,3-trimethyl- | C7H16 | 192509342 | 2.37% |
| 2.322 | Hexane, 2-methyl- | C7H16 | 260088595 | 3.21% |
| 2.362 | Pentane, 2,3-dimethyl- | C7H16 | 214293317 | 2.64% |
| 2.435 | Hexane, 3-methyl- | C7H16 | 118247949 | 1.46% |
| 3.372 | Hexane, 2,4-dimethyl- | C8H18 | 277742629 | 3.42% |
| 3.572 | Hexane, 3,3-dimethyl- | C8H18 | 411076226 | 5.07% |
| 3.956 | Pentane, 2,3,3-trimethyl- | C8H18 | 427008978 | 5.26% |
| 4.092 | Hexane, 2,3-dimethyl- | C8H18 | 270109110 | 3.33% |
| 6.015 | Hexane, 2,3,5-trimethyl- | C9H20 | 554883957 | 6.84% |
| 7.000 | Hexane, 2,3,3-trimethyl- | C9H20 | 765085303 | 9.43% |
| 7.833 | Heptane, 2,3-dimethyl- | C9H20 | 395838714 | 4.88% |
| 8.161 | Octane, 4-methyl- | C9H20 | 317981185 | 3.92% |
| 8.481 | Octane, 3-methyl- | C9H20 | 216602963 | 2.67% |
| 8.649 | Heptane, 2,2,4-trimethyl- | C10H22 | 150153351 | 1.85% |
| 9.090 | Octane, 2,4,6-trimethyl- | C11H24 | 144791181 | 1.79% |
| 9.739 | 4,4-Dimethyl octane | C10H22 | 265381045 | 3.27% |
| 10.403 | Heptane, 2,3,5-trimethyl- | C10H22 | 285161227 | 3.52% |
| 10.836 | Octane, 2,5-dimethyl- | C10H22 | 112618597 | 1.39% |
| 11.18 | Hexane, 4-ethyl-2-methyl- | C9H20 | 137825010 | 1.70% |
| 11.717 | Heptane, 2,3,5-trimethyl- | C10H22 | 265334471 | 3.27% |
| 12.149 | Undecane, 2,6-dimethyl- | C13H28 | 138272302 | 1.70% |
| 13.054 | Octane, 2,3,3-trimethyl- | C11H24 | 153331788 | 1.89% |
| 14.552 | Octane, 3,4,5,6-tetramethyl- | C12H26 | 80912092 | 1.00% |
| 14.952 | Nonane, 3-methyl- | C10H22 | 129050313 | 1.59% |
| 15.361 | Decane, 3,6-dimethyl- | C12H26 | 210633710 | 2.60% |
| 16.674 | Decane, 2,5,9-trimethyl- | C13H28 | 65315712 | 0.81% |

TABLE 4-continued

| Retention Time (min) | Spectral Match | Mass/Formula | Area | Percent |
|---|---|---|---|---|
| 17.451 | Octane, 2,3,6,7-tetramethyl- | C12H26 | 325298855 | 4.01% |
| 19.293 | Undecane, 5,7-dimethyl- | C13H28 | 124689436 | 1.54% |
| 21.440 | Decane, 2,3,6-trimethyl- | C13H28 | 39714150 | 0.49% |
| | Total | | 8111227610 | |

Example 3

Figure 14A:
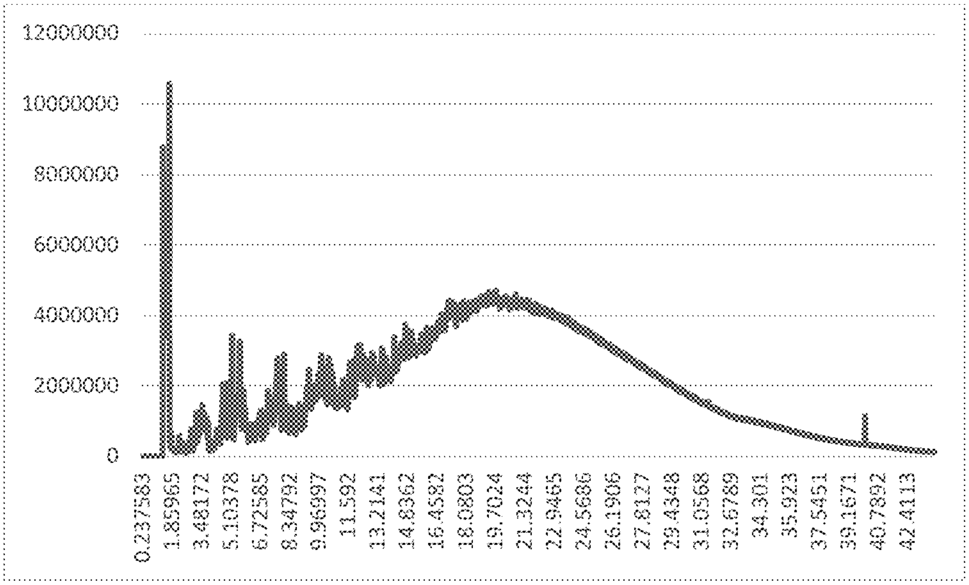
FIG. 14A and FIG. 14B are chromatograms of products stream samples S5 and S6 respectively, obtained according to Example 3.

A device according to FIG. 1 having a longitudinal electrode configuration according to FIG. 7 was operated at the following parameters: 440 Hz; 24,600 VAC sec voltage; atmospheric pressure; and ambient temperature. The gas phase hydrocarbon input was propane. A product stream sample S5 was collected and analyzed by gas chromatography. The GC output for sample S5 is provided in FIG. 14A. Compounds identified in the GC chromatogram for sample S5 are provided in Table 5.

TABLE 5

| RT | Area | Name |
|---|---|---|
| 1.4254 | 57.8044 | Acetone |
| 1.7951 | 11.8393 | Acetone |
| 4.6696 | 2.8051 | Hexane, 2,3,5-trimethyl- |
| 4.9064 | 1.953 | Heptane, 2,4-dimethyl- |
| 5.0464 | 1.7889 | Trichloroacetic acid, 4-methylpentyl ester |
| 5.1648 | 3.5609 | Pentane, 3-ethyl-2,4-dimethyl- |
| 5.6493 | 3.5684 | Pentane, 3-ethyl-2,4-dimethyl- |
| 5.8861 | 3.598 | Octane, 4-methyl- |
| 6.245 | 2.2575 | Allyl methallyl ether |
| 8.1111 | 10.8245 | Octane, 2,5,6-trimethyl- |

Figure 14B:
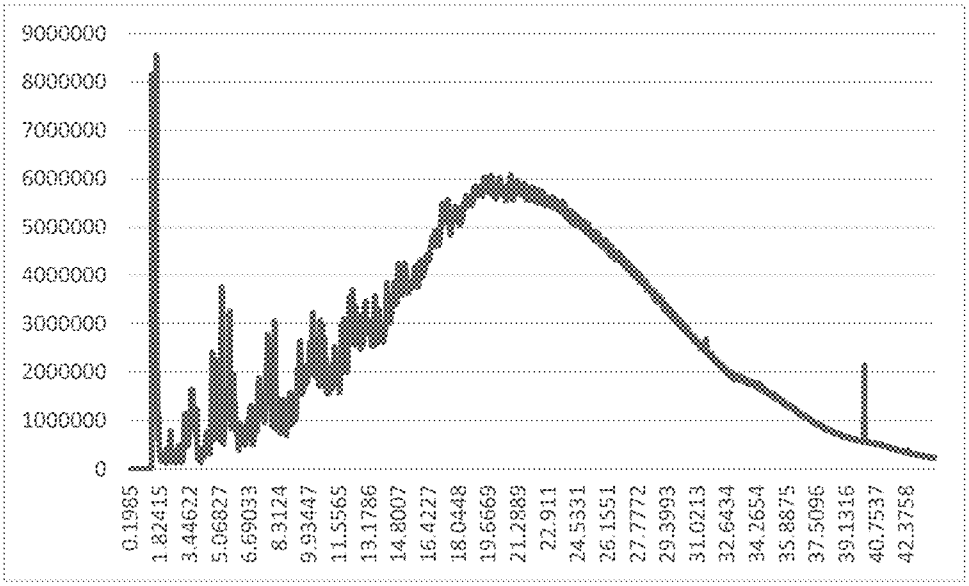

A second experiment under conditions indicated above for Example 3 was performed. A product stream sample S6 was collected and analyzed by gas chromatography. The GC output for sample S6 is provided in FIG. 14B. Compounds identified in the GC chromatogram for sample S6 are provided in Table 6.

TABLE 6

| RT | Area | Name |
|---|---|---|
| 1.4473 | 40.4976 | Acetone |
| 1.7021 | 10.3522 | Acetone |
| 3.213 | 2.8166 | 3-Pentanol, 2,2-dimethyl- |
| 3.8948 | 2.164 | Heptane, 3-methyl- |
| 4.7238 | 6.9858 | Hexane, 2,3,5-trimethyl- |
| 4.8853 | 2.4631 | Heptane, 2,4-dimethyl- |
| 5.2369 | 14.0658 | Hexane, 2,3,5-trimethyl- |
| 5.6353 | 3.289 | Pentane, 3-ethyl-2,4-dimethyl- |
| 5.8757 | 2.9051 | Octane, 4-methyl- |
| 6.231 | 1.6455 | 1-Octanol, 3,7-dimethyl-, (S)- |
| 8.1258 | 8.9646 | Nonane |

While various embodiments of the invention have been described above, it should be understood that they have been presented by way of example only, and not by way of limitation. Likewise, the various diagrams may depict an example architectural or other configuration for the disclosure, which is done to aid in understanding the features and functionality that can be included in the disclosure. The disclosure is not restricted to the illustrated example architectures or configurations, but can be implemented using a variety of alternative architectures and configurations. Additionally, although the disclosure is described above in terms of various exemplary embodiments and implementations, it should be understood that the various features and functionality described in one or more of the individual embodiments are not limited in their applicability to the particular embodiment with which they are described. They instead can be applied, alone or in some combination, to one or more of the other embodiments of the disclosure, whether or not such embodiments are described, and whether or not such features are presented as being a part of a described embodiment. Thus the breadth and scope of the present disclosure should not be limited by any of the above-described exemplary embodiments.

It will be appreciated that, for clarity purposes, the above description has described embodiments with reference to different functional units. However, it will be apparent that any suitable distribution of functionality between different functional units may be used without detracting from the invention. For example, functionality illustrated to be performed by separate computing devices may be performed by the same computing device. Likewise, functionality illustrated to be performed by a single computing device may be distributed amongst several computing devices. Hence, references to specific functional units are only to be seen as references to suitable means for providing the described functionality, rather than indicative of a strict logical or physical structure or organization.

Embodiments of the present disclosure are described above and below with reference to flowchart illustrations of methods, apparatus, and computer program products. It will be understood that each block of the flowchart illustrations, and combinations of blocks in the flowchart illustrations, can be implemented by execution of computer program instructions. These computer program instructions may be loaded onto a computer or other programmable data processing apparatus (such as a controller, microcontroller, microprocessor or the like) in a sensor electronics system to produce a machine, such that the instructions which execute on the computer or other programmable data processing apparatus create instructions for implementing the functions specified in the flowchart block or blocks. These computer program instructions may also be stored in a computer-readable memory that can direct a computer or other programmable data processing apparatus to function in a particular manner, such that the instructions stored in the computer-readable memory produce an article of manufacture including instructions which implement the function specified in the flowchart block or blocks. The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions specified in the flowchart block or blocks presented herein.

All references cited herein are incorporated herein by reference in their entirety. To the extent publications and patents or patent applications incorporated by reference contradict the disclosure contained in the specification, the specification is intended to supersede and/or take precedence over any such contradictory material.

Unless otherwise defined, all terms (including technical and scientific terms) are to be given their ordinary and customary meaning to a person of ordinary skill in the art, and are not to be limited to a special or customized meaning unless expressly so defined herein. It should be noted that the use of particular terminology when describing certain features or aspects of the disclosure should not be taken to imply that the terminology is being re-defined herein to be restricted to include any specific characteristics of the features or aspects of the disclosure with which that terminology is associated. Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof; adjectives such as 'known', 'normal', 'standard', and terms of similar meaning should not be construed as limiting the item described to a given time period or to an item available as of a given time, but instead should be read to encompass known, normal, or standard technologies that may be available or known now or at any time in the future; and use of terms like 'preferably,' 'preferred,' 'desired,' or 'desirable,' and words of similar meaning should not be understood as implying that certain features are critical, essential, or even important to the structure or function of the invention, but instead as merely intended to highlight alternative or additional features that may or may not be utilized in a particular embodiment of the invention. Likewise, a group of items linked with the conjunction 'and' should not be read as requiring that each and every one of those items be present in the grouping, but rather should be read as 'and/or' unless expressly stated otherwise. Similarly, a group of items linked with the conjunction 'or' should not be read as requiring mutual exclusivity among that group, but rather should be read as 'and/or' unless expressly stated otherwise.

Where a range of values is provided, it is understood that the upper and lower limit, and each intervening value between the upper and lower limit of the range is encompassed within the embodiments.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

All numbers expressing quantities of ingredients, reaction conditions, and so forth used in the specification are to be understood as being modified in all instances by the term 'about.' Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

Furthermore, although the foregoing has been described in some detail by way of illustrations and examples for purposes of clarity and understanding, it is apparent to those skilled in the art that certain changes and modifications may be practiced. Therefore, the description and examples should not be construed as limiting the scope of the invention to the specific embodiments and examples described herein, but rather to also cover all modification and alternatives coming with the true scope and spirit of the invention.

What is claimed is:

1. A method for hydrocarbon conversion, comprising:

introducing a first gaseous hydrocarbon having a first molecular weight into a vessel, the vessel comprising an outlet and a liquid level controller coupled to a liquid control valve, and wherein the vessel is charged or grounded;

maintaining, via manipulation of the liquid control valve by the liquid level controller, a liquid level within the vessel so that the outlet of the vessel is located at a level below a liquid gas interface of the vessel, and subjecting the first gaseous hydrocarbon to an electric field to create a plasma in the vessel, whereby at least a portion of the first gaseous hydrocarbon is converted to a second hydrocarbon having a second molecular weight.

2. The method of claim 1, wherein the second molecular weight is greater than the first molecular weight.

3. The method of claim 2, wherein the heavier hydrocarbon is a liquid hydrocarbon.

4. The method of claim 1, wherein the electric field is variable frequency electric field.

5. The method of claim 4, further comprising adjusting a frequency of the variable frequency electric field to adjust a rate of conversion of the first gaseous hydrocarbon to the second hydrocarbon.

6. The method of claim 4, further comprising:

measuring a characteristic of a product formed in the vessel, the product comprising the second hydrocarbon; and adjusting a frequency of the variable frequency electric field in response to the measured characteristic.

7. The method of claim 1, further comprising subjecting the first gaseous hydrocarbon to a variable voltage electric field.

8. The method of claim 7, further comprising adjusting a voltage of the variable voltage electric field to adjust a rate of conversion of the first gaseous hydrocarbon to the second hydrocarbon.

9. The method of claim 7, further comprising:

measuring a characteristic of a product formed in the vessel, the product comprising the second hydrocarbon; and adjusting a voltage of the variable voltage electric field in response to the measured characteristic.

10. The method of claim 1, further comprising subjecting the first gaseous hydrocarbon to a variable frequency and a variable voltage electric field.

11. The method of claim 10, further comprising adjusting a frequency and a voltage of the variable frequency and variable voltage electric field to adjust a rate of conversion of the first gaseous hydrocarbon to the second hydrocarbon.

12. The method of claim 1, further comprising introducing the first gaseous hydrocarbon introduced into the vessel at a controlled rate based on conversion of the first gaseous hydrocarbon to the second hydrocarbon.

13. The method of claim 1, wherein an amount of the first gaseous hydrocarbon introduced into the vessel is controlled based on a pressure within the vessel.

14. The method of claim 1, wherein the electric field is an oscillating electric field.

15. The method of claim 14, wherein the electric field oscillates at a frequency from 60 to 1000 Hz.

16. The method of claim 1, wherein the vessel comprises an electrode covered with an insulating material having dielectric properties.

17. The method of claim 1, further comprising applying an alternating current to one or more electrodes to form the electric field.

18. A method for hydrocarbon conversion, comprising:

introducing a first gaseous hydrocarbon having a first molecular weight into a vessel, wherein the vessel is charged or grounded; and subjecting the first gaseous hydrocarbon to an electric field to create a plasma in the vessel, whereby at least a portion of the first gaseous hydrocarbon is converted to a second hydrocarbon having a second molecular weight, wherein the vessel comprises one or more powered electrodes and one or more grounded electrodes, wherein the vessel comprises a different number of powered electrodes than grounded electrodes.

19. The method of claim 18, further comprising:

subjecting the first gaseous hydrocarbon to a variable frequency and a variable voltage electric field;

measuring a characteristic of a product formed in the vessel, the product comprising the heavier hydrocarbon; and adjusting a frequency or a voltage of the variable frequency and variable voltage electric field in response to the measured characteristic.

* * * * *